(12) United States Patent
Burbank et al.

(10) Patent No.: US 6,471,700 B1
(45) Date of Patent: Oct. 29, 2002

(54) APPARATUS AND METHOD FOR ACCESSING BIOPSY SITE

(75) Inventors: Fred Burbank; William C. Homet, both of San Juan Capistrano; Paul Lubock, Laguna Niguel; Richard L. Quick, Mission Viejo; Martin Shabaz, Lake Forest, all of CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

(21) Appl. No.: 09/477,255

(22) Filed: Jan. 4, 2000

Related U.S. Application Data

(63) Continuation-in-part of application No. 09/343,975, filed on Jun. 30, 1999, now Pat. No. 6,347,241, which is a continuation-in-part of application No. 09/654,920, filed on Sep. 5, 2000, which is a division of application No. 09/241,936, filed on Feb. 2, 1999, now Pat. No. 6,161,034, which is a continuation-in-part of application No. 09/159,467, filed on Sep. 23, 1998, now Pat. No. 6,261,241, and a continuation-in-part of application No. 09/057,303, filed on Apr. 8, 1998, now Pat. No. 6,331,166.

(51) Int. Cl.$^7$ ............................................. A61B 18/18
(52) U.S. Cl. ......................... 606/45; 606/41; 600/562
(58) Field of Search ................................ 600/562–564; 606/41, 45, 46, 47–50

(56) References Cited

U.S. PATENT DOCUMENTS

| | | | |
|---|---|---|---|
| 4,362,160 A | 12/1982 | Hiltebrandt |
| 4,565,200 A | 1/1986 | Cosman |
| 4,909,250 A | 3/1990 | Smith |
| 5,047,027 A | 9/1991 | Rydell |

(List continued on next page.)

FOREIGN PATENT DOCUMENTS

| | | |
|---|---|---|
| DE | 12 25 813 | 9/1966 |
| EP | 0 983 749 | 3/2000 |
| WO | WO 98 06346 | 2/1998 |
| WO | WO 98 08441 | 3/1998 |
| WO | WO 99/44506 | 9/1999 |
| WO | WO 00/16697 | 3/2000 |

OTHER PUBLICATIONS

Stereotactic Breast Biopsy: Its History, Its Present, and Its Future, F. Burbank, M.D., *The American Surgeon*, Feb. 1996, vol. 62, pp. 128–150.

Percutaneous Biopsy Techniques, Timothy J. Micklos, *Manual of Oncologic Thrapeutics*, (1989/1990), pp. 39–42.

Coaxial Core Needle Biopsy Under Mammographic Guidance: Indications and Applications, Whitman wt al., AJR. 171, Jul. 1998, pp. 67–70.

*Primary Examiner*—Roy D. Gibson
(74) *Attorney, Agent, or Firm*—Coudert Brothers LLP

(57) ABSTRACT

A system for accessing a desired site within a patient's body includes a cannula defining an inner lumen that opens into a longitudinally extending side aperture formed in the side of the cannula, near its distal end. An electrosurgical stylet slidably fits inside the inner lumen. At the distal end of the stylet is an electrosurgical electrode capable of ablating tissue and permitting advancement of the system into a patient's body. The electrode, in an expanded deployed configuration, can be wider than the maximum transverse dimension of the cannula, but it may be deflected toward the center of the stylet so that the electrode fits within the inner lumen of the cannula, permitting the stylet to be inserted and removed through the cannula. An elongate guide tube having a central axial bore which communicates with an orifice in the side of the guide tube can be inserted into the inner lumen of the cannula such that the guide tube orifice coincides with the longitudinally extending side aperature of the cannula. In use, the stylet with the cannula disposed about it is advanced into the patient's tissue, using electrosurgical ablation, until the side aperture of the cannula is disposed adjacent a desired site within the patient. The stylet can then be withdrawn from the cannula providing access through the inner lumen of the cannula to the tissue at the desired site.

33 Claims, 22 Drawing Sheets

U.S. PATENT DOCUMENTS

| | | |
|---|---|---|
| RE34,056 E | 9/1992 | Lindgren et al. |
| 5,395,319 A | 3/1995 | Hirsh et al. |
| 5,415,656 A | 5/1995 | Tihon et al. |
| 5,417,687 A * | 5/1995 | Nardella et al. .............. 606/32 |
| 5,437,665 A * | 8/1995 | Munro ........................ 606/47 |
| 5,470,308 A | 11/1995 | Edwards et al. |
| 5,487,385 A * | 1/1996 | Avitall ........................ 600/374 |
| 5,526,822 A | 6/1996 | Burbank et al. |
| 5,538,010 A | 7/1996 | Darr et al. .................. 128/754 |
| 5,607,389 A | 3/1997 | Edwards et al. |
| 5,649,547 A | 7/1997 | Ritchart et al. |
| 5,687,739 A | 11/1997 | McPherson et al. |
| 5,720,763 A * | 2/1998 | Tovey ........................ 606/198 |
| 5,772,660 A | 6/1998 | Young et al. |
| 5,775,333 A | 7/1998 | Burbank et al. |
| 5,782,764 A * | 7/1998 | Werne ........................ 600/411 |
| 5,782,775 A | 7/1998 | Milliman et al. |
| 5,794,626 A | 8/1998 | Kieturakis |
| 5,797,907 A | 8/1998 | Clement |
| 5,800,378 A * | 9/1998 | Edwards et al. .............. 602/22 |
| 5,853,366 A | 12/1998 | Dowlatshahi |
| 5,876,340 A * | 3/1999 | Tu et al. ..................... 600/439 |
| 5,902,272 A | 5/1999 | Eggers et al. |
| 5,925,044 A | 7/1999 | Hofmann et al. |
| 5,928,164 A | 7/1999 | Burbank et al. |
| 5,964,716 A * | 10/1999 | Gregoire et al. ............ 600/564 |
| 5,972,002 A * | 10/1999 | Bark et al. .................. 606/140 |
| 5,984,919 A * | 11/1999 | Hilal et al. ................... 606/45 |
| 6,004,269 A * | 12/1999 | Crowley et al. ............ 600/439 |
| 6,050,955 A | 4/2000 | Bryan et al. ................ 600/566 |
| 6,056,700 A | 5/2000 | Burney et al. |
| 6,063,082 A * | 5/2000 | DeVore et al. ................ 606/45 |
| 6,142,955 A | 11/2000 | Farascioni et al. .......... 600/562 |
| 6,161,034 A | 12/2000 | Burbank et al. |

\* cited by examiner

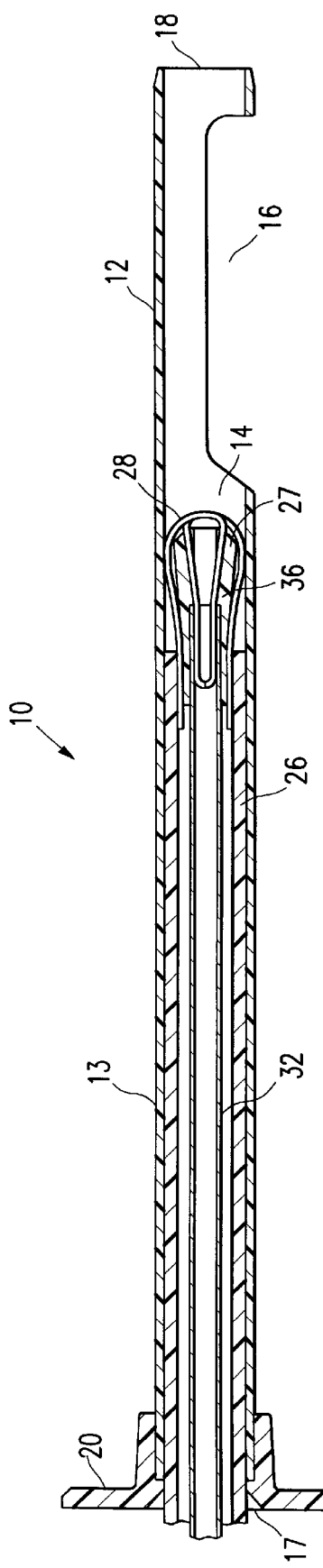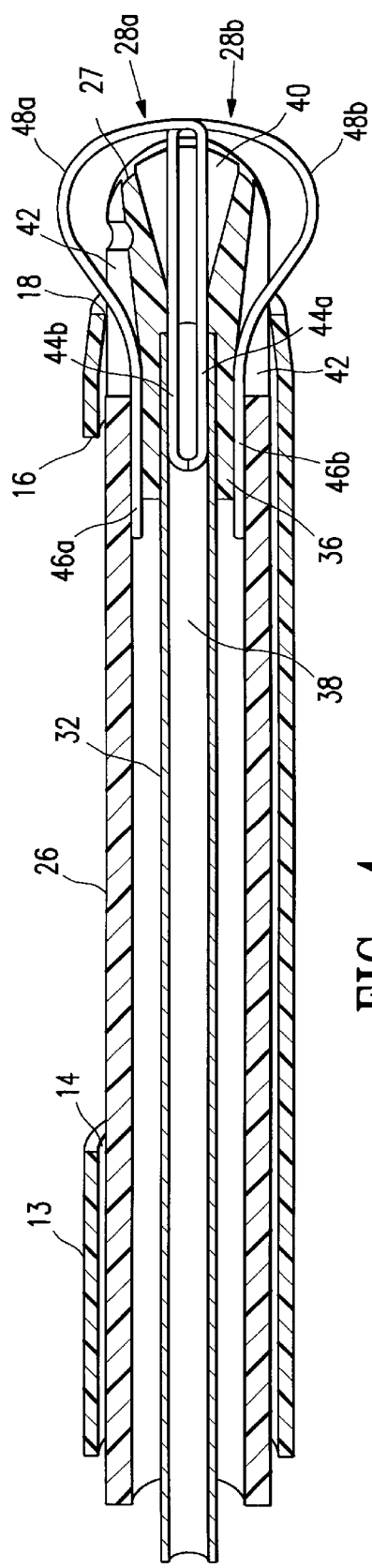

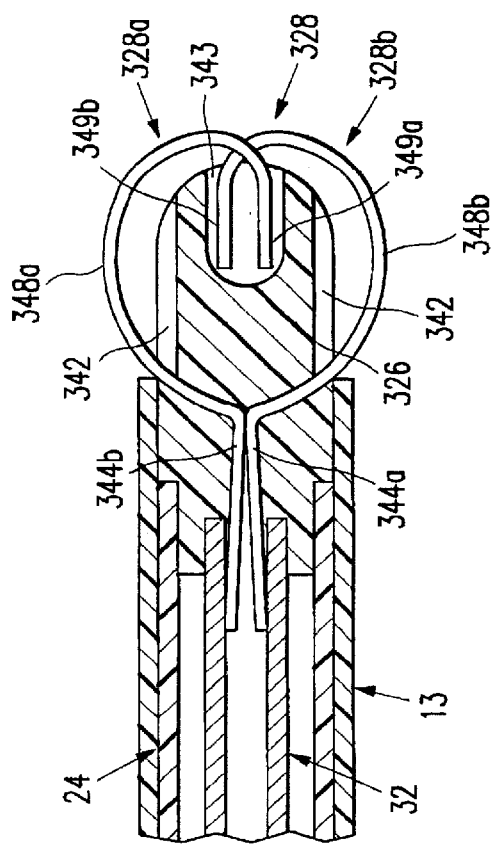
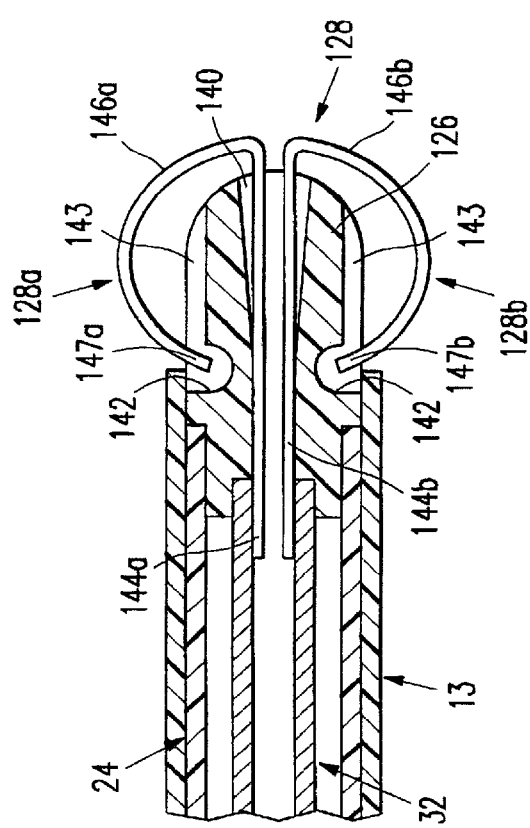
FIG. 4A  FIG. 4B  FIG. 4C

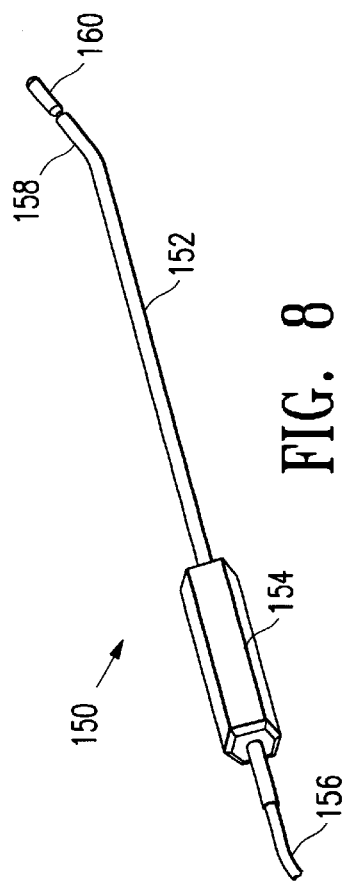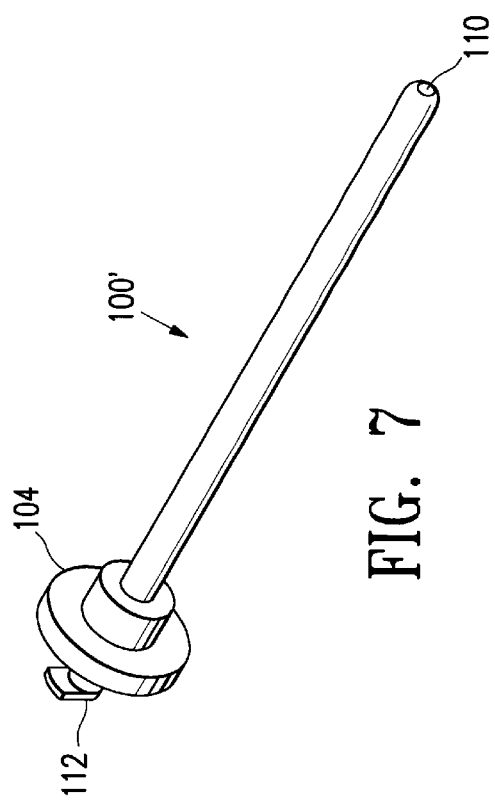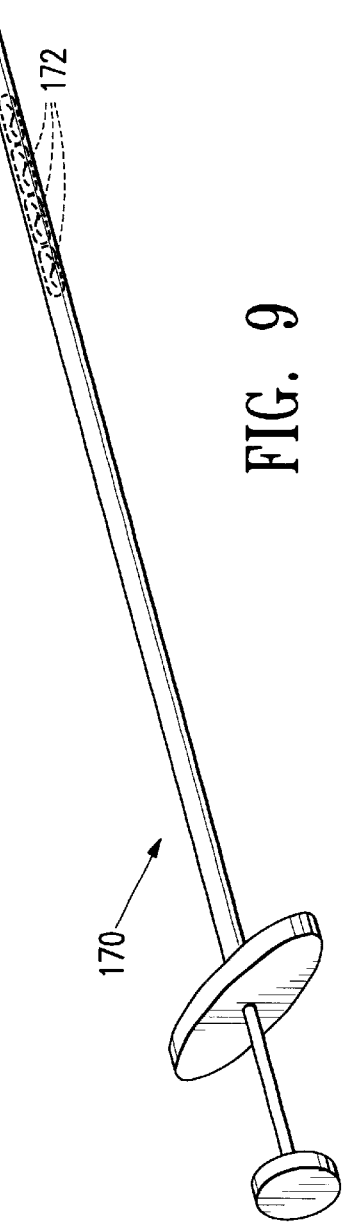

APPARATUS AND METHOD FOR ACCESSING BIOPSY SITE

This application is a continuation-in-part of application Ser. No. 09/343,975, filed Jun. 30, 1999, now U.S. Pat. No. 6,347,241 which is a continuation-in-part of application Ser. No. 09/654,920, filed Sep. 5, 2000, which is a divisional of application Ser. No. 09/241,936, filed Feb. 2, 1999, now U.S. Pat. No. 6,161,034; a continuation-in-part of application Ser. No. 09/159,467, filed Sep. 23, 1998, now U.S. Pat. No. 6,261,241; and a continuation-in-part of application Ser. No. 09/057,303, filed Apr. 8, 1998, now U.S. Pat. No. 6,331,166, all of the specifications of which are hereby incorporated by reference in their entirety and from all of which priority is hereby claimed under 35 U.S.C. §120.

BACKGROUND OF THE INVENTION

The present invention relates generally to the field of surgical biopsy instruments and methods. More specifically, it relates to a device and method for electrosurgically accessing a pathologically suspect tissue mass in a patient's body, so as to facilitate the taking of a biopsy sample of the tissue mass, and to facilitate subsequent surgical procedures in the region of the tissue mass.

In diagnosing and treating certain medical conditions, such as potentially cancerous tumors, it may be desirable to perform a biopsy, in which a specimen of the suspicious tissue is removed for pathological examination and analysis. In many instances, the suspicious tissue is located in a subcutaneous site, such as inside a human breast. To minimize surgical intrusion into patient's body, it is desirable to be able to insert a small instrument into the body for extracting the biopsy specimen.

After removing the tissue samples, additional procedures may be performed at the biopsy site. For example, it may be necessary to cauterize or otherwise treat the resulting cavity to stop bleeding and reduce the risk of infection or other complications. Also, it may be advantageous to mark the site for future surgical procedures should pathological tests performed on the biopsy specimen indicate surgical removal or other treatment of the suspected tissue mass from which the specimen was removed. Such marking can be performed, for example, by the apparatus and method disclosed and claimed in co-pending U.S. patent application Ser. No. 09/343,975, filed Jun. 30, 1999, entitled "Biopsy Site Marker and Process and Apparatus for Applying It," which is hereby incorporated by reference in its entirety.

Electrosurgical techniques have been used in a variety of circumstances, including certain types of biopsy procedures. In electrosurgery, high frequency electrical energy is applied through a primary electrode to patient tissue. The electrical energy flows through the tissue to a return electrode that is in contact with the patent's tissue. Typically, the return electrode is attached to the patient at a point remote from where the primary electrode contacts the tissue. The tissue adjacent the primary electrode is ablated, to form an opening in the tissue. An electrosurgical biopsy instrument is disclosed and claimed in U.S. patent application Ser. No. 09/159,467 for "Electrosurgical Biopsy Device and Method," assigned to the assignee of the subject application, and which is hereby incorporated by reference in its entirety.

Existing electrosurgical devices have an outer cannula with an elongated hollow outer tube through which a stylet may be inserted and then removed. The stylet is designed so that, when the stylet is fully inserted through the cannula, the distal end of the stylet and electrode disposed thereon, extends beyond the distal end of the cannula. When the stylet is fully inserted through the cannula, the electrode is exposed beyond the end of the cannula. When electrically activated, the electrode ablates the tissue adjacent the electrode, to produce a tissue opening slightly larger than the width of the primary electrode itself. As the primary electrode ablates the tissue, the operator can insert the stylet and the surrounding cannula into the tissue opening until the cannula is inserted to the desired point. However, the width of the electrode has been limited by the inner diameter of the cannula through which it is inserted. Consequently, the tissue opening created by the primary electrode may be smaller than the cannula. What has been needed is a stylet having an electrode that can be inserted through the inside diameter of a cannula yet ablate a passage in tissue large enough for the cannula to easily pass through.

SUMMARY

The present invention is directed to a system, specifically a biopsy system, which gives ready access to a desired site or subcutaneous target tissue site within a patient's body. In one embodiment, the system includes an electrosurgical stylet having an elongate shaft with a proximal end and a distal end. At the distal end of the elongate shaft is an electrosurgical electrode. The electrosurgical electrode has an expanded deployed configuration which is wider than a maximum outside transverse dimension of the elongate shaft, and a constricted configuration which has a width not greater than an outside transverse dimension of the elongate shaft. Another embodiment of the system includes a cannula having a proximal end, a distal end and an inner lumen extending between and in fluid communication with proximal and distal openings. The electrosurgical stylet can be slidably received inside the inner lumen. The electrode of the stylet may be deflected radially inward toward a longitudinal axis of the elongate shaft so that the electrode has a width which is less than an inside transverse dimension of the inner lumen. In this way, the electrode fits within the inner lumen of the cannula, permitting the stylet to be inserted and removed through the cannula. The stylet can be configured to extend distally relative to the cannula to an extended position with the electrode extending distally beyond the distal opening of the cannula and the stylet disposed within the inner lumen of the cannula. The cannula may also have a longitudinally extending side aperature in fluid communication with the inner lumen and disposed proximally of the distal end of the cannula and distially of the proximal end of the cannula.

The electrode may be formed of two or more electrode portions or a single portion extending from and about the distal end of the elongate shaft of the stylet. An electrical conductor extending the length of the stylet provides electrical contact between the proximal end of the stylet and the electrode. In one embodiment, the electrode has a first and second electrode portions that are resiliently deflectable in an inward radial direction when the electrode is resiliently deformed from the expanded deployed configuration to the contracted configuration. The electrode may form an arcuate cutting element which is disposed distally of the distal end of the elongate shaft and which can lie in a plane which is substantially parallel to a longitudinal axis of the elonagate shaft. In some embodiments, the electrode has a width substantially equal to or greater than one half the circumference of the distal end of the cannula. In this way, the system will easily penetrate tissue behind such an activated electrode which is ablating tissue and creating a hole or passage with a circumference which is substantially equal to or greater than the circumference of the cannula.

In another embodiment of the invention, a hand grip is disposed on the proximal end of the elongate shaft of the stylet, and the proximal end of the cannula is provided with a peripheral flange. The hand grip can include a locking lever having a distal end that releasably engages the flange of the cannula. Thus, the stylet and the cannula can be locked together when the locking lever engages the flange to prevent relative axial movement between the cannula and the stylet. When it is desired to remove the stylet from the cannula, the locking lever is actuated to disengage its distal end of the locking lever from the flange, thereby allowing removal of the stylet.

In yet another embodiment of a system having features of the invention, a guide tube is configured to be slidably disposed in the inner lumen of the cannula. A central bore can extend along almost the entire length of the guide tube, except that near the distal end of the guide tube, the bore curves to communicate with a guide tube side orifice in the side of the guide tube. Alternatively, the bore may extend the entire length of the guide tube, terminating in an orifice at the distal end of the guide tube. The guide tube is dimensioned so that, when it is fully inserted into the cannula, the guide tube side orifice coincides with the longitudinally extending side aperture of the cannula.

The guide tube bore is internally dimensioned to permit the passage through it of an electrocautery device that may be inserted through the bore of the guide tube to cauterize the biopsy cavity, following the taking of a biopsy sample or other suitable procedure. Similarly, a marker insertion device may also be inserted through the central bore of the guide tube to insert temporary or permanent markers into a biopsy cavity or any other desired site within a patient's body.

In accordance with a biopsy procedure of the present invention, the electrosurgical stylet with the cannula surrounding it is inserted into tissue of a patient, using electrosurgical techniques, until the side aperture of the cannula is disposed adjacent a desired site within the patient or a targeted tissue site. The electrosurgical stylet is then withdrawn from the cannula while leaving the cannula in place in the patient's tissue. A biopsy device can then be inserted through the inner lumen of the cannula to obtain one or more samples of tissue from the targeted site. Alternatively, any desired amount of tissue could be removed so as to complete any necessary surgical intervention, such as removal of a tumor or the like. After the samples have been taken, the biopsy device is removed, again leaving the cannula in place. The guide tube may then be placed into the cannula so that the guide tube orifice coincides with or is disposed adjacent to the longitudinally extending side aperture of the cannula. A cauterization instrument, such as an electrocautery device, may be inserted through the central bore of the guide tube, and activated to cauterize the biopsy cavity. Finally, a marker installation device may be inserted through the guide tube to insert temporary and/or permanent markers at the biopsy site to identify the location from which the biopsy samples were taken. This enables a physician to easily locate the surgical site within the patient subsequent to the procedure if further intervention becomes necessary or for any other reason that it may be necessary to identify the surgical site.

In an alternative embodiment of the invention, a cannula is used that is substantially shorter than the stylet and lacks a side aperture. The system is advanced into the patient's tissue with the stylet inserted into the cannula and with a tubular spacer element disposed on the proximal end of the cannula. The cannula and the stylet are advanced into the body of the patient to a desired site therein. When the stylet is withdrawn, leaving the cannula in place, a biopsy device can be inserted through the tubular spacer element and the stylet. The spacer element is then removed, and the cannula is moved proximally along the biopsy device to expose the target tissue site to the tissue sampling or other active portion of the biopsy device.

BRIEF DESCRIPTION OF THE DRAWINGS

FIG. 3A is a longitudinal cross-sectional of the cannula and stylet of FIG. 2, showing the stylet in a retracted position;

FIG. 4 is a longitudinal cross-sectional view of a distal end portion of the cannula and stylet illustrated in FIG. 3, showing the stylet in its extended position;

FIGS. 4A through 4E are cross-sectional views of additional embodiments of a distal end portion of a cannula and electrosurgical stylet having features of the present invention;

FIG. 7 is a perspective view of an embodiment of a guide tube that may be used in the present invention;

FIG. 8 is a perspective view of an electrocautery device that may be employed with the present invention;

FIG. 9 is a perspective view of a biopsy marker insertion device that may be used in conjunction with the guide tubes illustrated in FIGS. 5 through 7;

DETAILED DESCRIPTION

Figure 1:
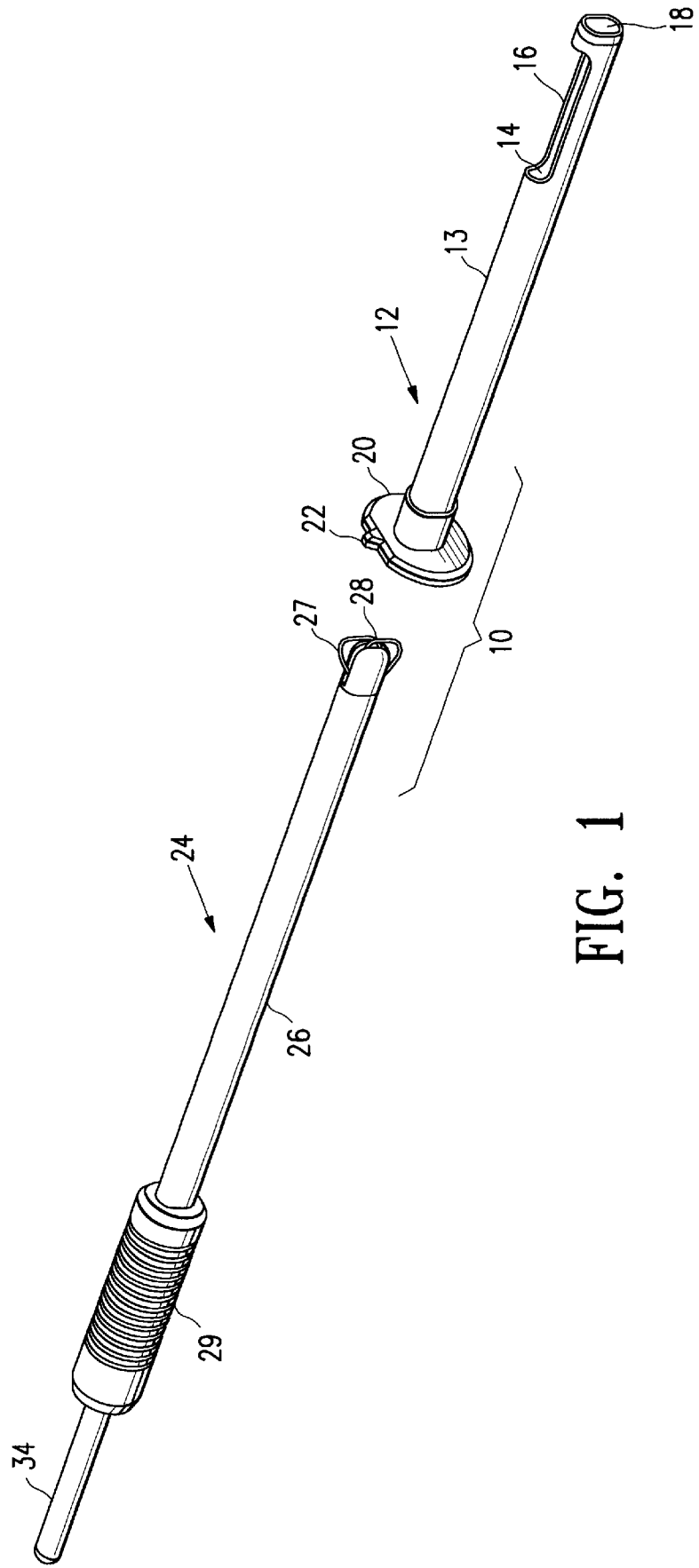
FIG. 1 is a perspective view of a cannula and an electrosurgical stylet having features of the present invention.

Reference is made to FIGS. 1, 2, 3, 3A, and 4, which illustrate a biopsy system representing an embodiment of the present invention. The system 10 includes a cannula 12 comprising an elongate, cannula barrel 13 that defines an inner lumen 14 that extends between a proximal opening 17 (FIG. 3A) and a distal opening 18. In the embodiment shown in FIG. 1, the cannula barrel 13 and inner lumen 14 are oblong in cross section, although other cross-sectional shapes, such as circular or pear shaped, may be appropriate, depending upon the types of instruments to be inserted through the inner lumen 14. A longitudinally extending side aperture 16 extends longitudinally along a portion of the length of the cannula barrel 13 near its distal end, communicating with the inner lumen 14. The cannula 12 can be formed of an electrically insulating, biocompatible material, such as a medical grade polymer (e.g., polycarbonate) or any other suitable material.

The proximal end of the cannula 12 is provided with an peripheral flange 20 surrounding the proximal opening 17. The flange 20 may include an indicator, such as an orientation point 22, that is aligned with the cannula side aperture 16 to provide the operator with a visual indication of the orientation of the cannula side aperture 16 when the cannula 12 is inserted into the patient. The peripheral flange 20 also advantageously includes an aperture 23, for receiving a locking lever which will be described below.

The system 10 may be inserted into a patient's tissue in conjunction with an electrosurgical stylet, as described below, until the side aperture 16 coincides with a desired site or a targeted tissue site (e.g., a suspected lesion or tumor), thereby providing access to the tissue site through the inner lumen 14. In one embodiment, the cannula barrel 13 can have a length of about 3 to about 15 cm, specifically, about 5 to about 13 cm, and more specifically, about 8 to about 9 cm. To assist in properly locating the cannula 12 during advancement of the system into a patient's body, (as described below), the cannula barrel 13 may be provided with indicators 25 adjacent one or both ends of the side aperture 16 that provide enhanced visualization by ultrasound. Thus, the indicators 25 are advantageously made of an echogenic polymer coating that increases contrast resolution in ultrasound imaging devices. A suitable coating for the indicators 25 is marketed under the trademark "ECHOC-OAT" by STS Biopolymers, of Henrietta, N.Y. In addition, the cannula barrel 13 is optionally coated with a lubricious coating such as a hydrophylic coating.

The system 10 also includes an electrosurgical stylet 24 that has an elongate shaft 26. The shaft 26 is externally dimensioned to be slidably received within the inner lumen 14. In one embodiment, the inner lumen 14 can have a major inside transverse dimension of about 3 to about 10 mm and a minor inside transverse dimension of about 2 to about 6 mm, specifically, a major inside transverse dimension of about 5 to about 6 mm and a minor inside transverse dimension of about 3.5 to about 4.5 mm. In addition, it may be desirable in some embodiments to have a close fit between the elongate shaft 26 and the inner lumen 14 to avoid a gap therebetween which can catch or snag on adjacent tissue during advancement through tissue and impede advancement. The stylet 24 may be formed of the same or a similar material as the cannula 12.

The stylet 24 has a distal end or head 27 from which an electrode 28 protrudes. The electrode 28, described in detail below, can be generally formed of conductive wire. When the electrode 28 is electrically activated with high frequency electrical energy and placed in contact with tissue, electrical energy flows through the tissue to a return electrode (not shown) that is also in contact with the patient. The tissue adjacent the primary electrode 28 is ablated to create an incision as the electrode 28 passes through the tissue. The electrode 28 can have a width in an expanded deployed configuration approximately equal to or slightly greater than one half the circumference of the cannula barrel at the maximum cross-sectional dimension of the cannula barrel 13, so that during the electrosurgical process, the electrode 28 makes an opening through the tissue sufficiently large to receive the cannula barrel 13. Electrode 28 is resiliently deflectable in an inward radial direction so that it may be constricted in width to a dimension less than an inside transverse dimension of the inner lumen 14, thereby permitting the elongate shaft 26 to be withdrawn through the inner lumen 14. Thus, when the elonagate shaft 24 is retracted into the cannula barrel 13, the electrode 28 resiliently contracts radially inward to fit inside the inner lumen 14, but when the distal end of the elongate shaft 26 is extended distally from the distal opening 18 of the cannula 12, a restoring spring force tends to expand the electrode 28 radially outward to an expanded deployed configuration having its full width. Thus, once the cannula 12 has been inserted into the patient by means of the incision or passage created by the electrode 28 on the stylet 24, the stylet 24 may be withdrawn from the cannula 12, leaving the cannula 12 in place in the patient.

Near the proximal end of the stylet 24 is a hand grip 29. In the illustrated embodiment, the hand grip 29 is substantially cylindrical, with an outside diameter that is larger than the diameter of the inner lumen 14, but less than the diameter of the peripheral flange 20. The hand grip 29 optionally includes a locking lever 30 having a distal end that terminates in a finger or projection 31 that extends in a radially inward direction. The finger 31 is dimensioned to pass through the flange aperture 23 and extend to the distal surface of the flange 20 when the stylet 24 is inserted into the cannula 12 in the fully deployed position. The locking lever 30 is mounted in the hand grip 29 for pivoting thereon, and it is biased, by means such as a biasing spring (not shown), so that the distal finger 31 is biased in a radially inward direction to engage the distal surface of the flange 20. Relative axial movement between the cannula and the stylet is thereby prevented when the stylet is deployed in the cannula. To withdraw the stylet 24 from the cannula 12, the proximal end of the locking lever 30 is depressed in an inward radial direction, causing the distal end to pivot in the radial outward direction, thereby disengaging the finger 31 from the distal surface of the flange 20, and allowing the finger 31 to pass back out through the flange aperture 23 in the proximal direction to release the stylet 24 from the cannula 12.

A tubular electrical conductor 32 (FIG. 3A) runs along a longitudinal axis of the elongate shaft 26 of the stylet 24 to the electrode 28 at the distal end 27 of the stylet 24. The electrical conductor 32 passes into a proximal stylet extension 34 for connection to an electrosurgical generator (not shown), of a type commonly used in electrosurgery.

Figure 2:
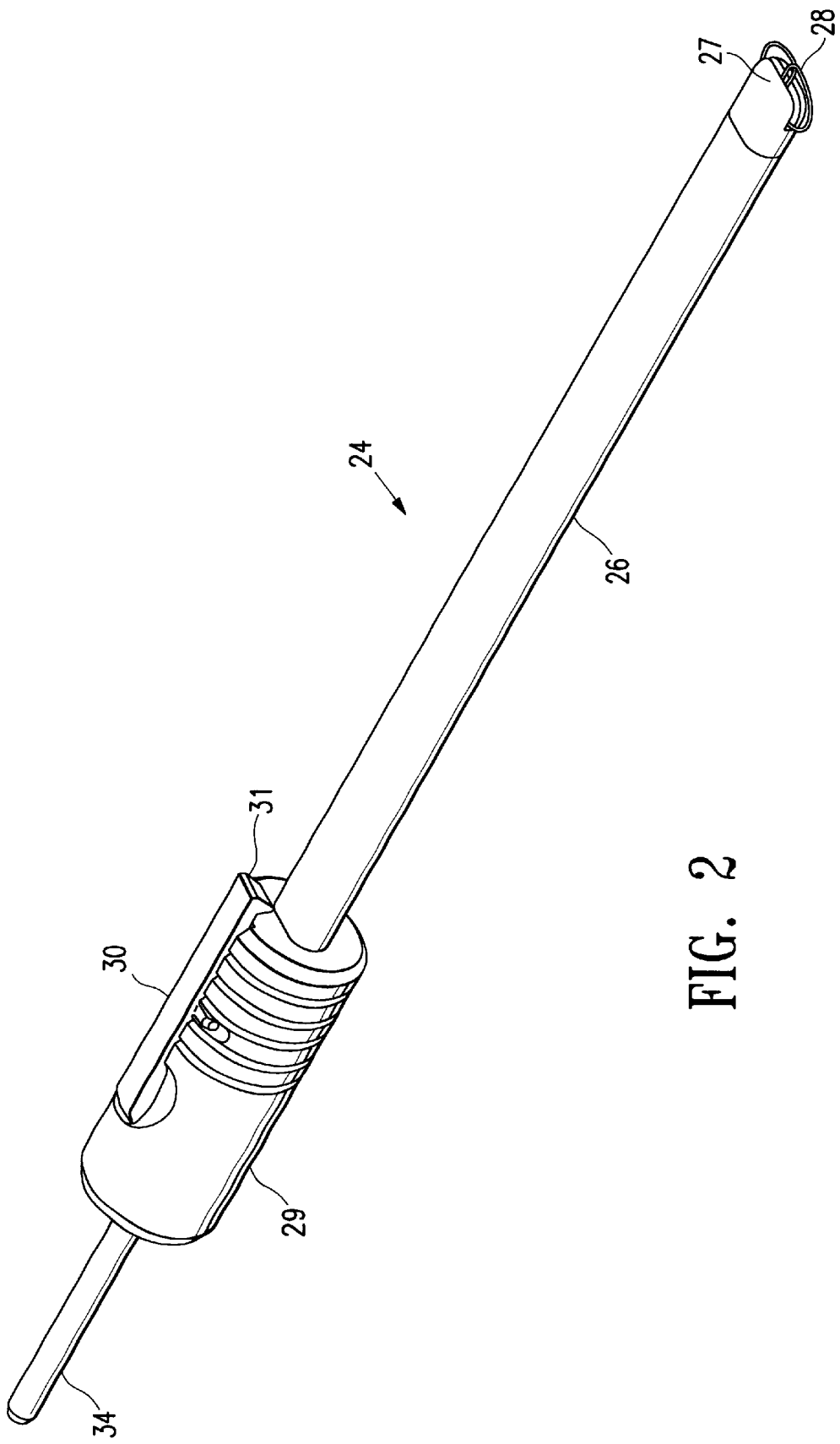
FIG. 2 is a perspective view of the stylet shown in FIG. 1.

Referring to FIG. 2, when the elongate shaft 26 is fully inserted into the cannula barrel 13, the distal end of the stylet hand grip 29 abuts against the proximal side of the cannula flange 20. The distal end or head 27 of the stylet 24, with the electrode 28, extends slightly beyond the distal opening 18 of the cannula barrel 13, so that the electrode 28 is released from the constraint provided by the inner lumen 14, and assumes its full width.

Figure 3:
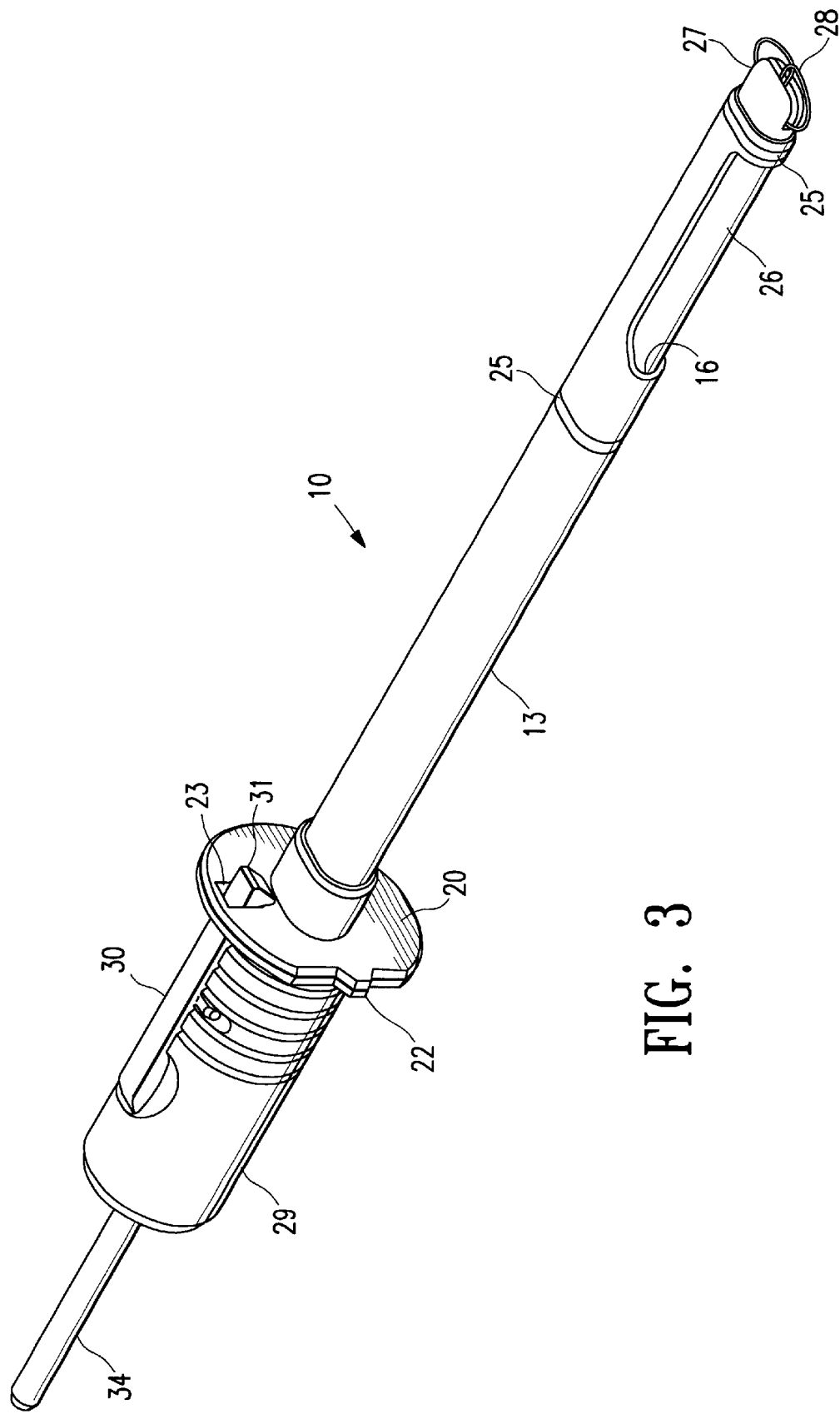
FIG. 3 is a perspective view of the cannula and stylet of FIG. 1, with the stylet slidably disposed within the cannula and in its extended position.

FIGS. 3 and 4 illustrate the distal portion of the cannula 12, with the elongate shaft 26 fully inserted through the cannula barrel 13, so that the stylet head 27 emerges from the distal opening 18 of the cannula barrel 13. The stylet head 27 has a tubular section 36 that fits inside the elongate shaft 26 and defines an axial bore 38 terminating in a central aperture 40 at the distal tip of the stylet head 27. A pair of diametrically-opposed side slots 42 are located proximally from the distal tip of the stylet head 27. The axial bore 38 receives the distal end of the tubular conductor 32.

The electrode 28, as shown in FIG. 3, is formed of a first and second electrode portions 28a, 28b. Each electrode portion 28a, 28b forms slightly over half the entire electrode width, with the two electrode portions 28a, 28b overlapping slightly in the middle. The electrode portions 28a, 28b have respective first or inner segments 44a, 44b that extend through the central aperture 40 and the axial bore 38, into the tubular conductor 32, to which they are electrically connected by welding, soldering or other suitable means. The first and second electrode portions 28a, 28b also include second or outer segments 46a, 46b, respectively, that are along side the inner wall of the stylet shaft 26, radially outwardly from tubular portion 36 of the stylet head 27. The second segments 46a, 46b emerge from the stylet head 27 through side slots 42. The first segments 44a, 44b are joined to their respective second segments 46a, 46b by outwardly-bowed segments 48a, 48b, respectively. The outwardly-bowed segments 48a, 48b are each formed into a curve that extends beyond the outer diameter of the distal tip of the stylet head 27, so that in its expanded deployed configuration illustrated in FIGS. 3 and 4, the maximum width of the electrode 28 (comprising the two electrode portions 28a, 28b) is greater than the maximum outside transverse dimension of the elongate shaft 26, and can be approximately equal to or slightly greater than one half the circumference of the cannula barrel at the maximum outside transverse dimension of the cannula barrel 13. In one embodiment, the maximum width of the electrode 28 is approximately 1.5 times the maximum outside transverse dimension of the cannula barrel 13.

The side slots 42 in the stylet head 27 provide recesses into which the bowed segments 48a, 48b of the electrode portions 28a, 28b, respectively, may be deflected. Inward pressure on either or both of the electrode portions 28a, 28b deflects them toward the center of the stylet head 27 and toward the longitudinal axis of the elongate shaft 26. The bowed segment of each electrode portion fits into the corresponding side slot 42 when such inward pressure is applied, so that the electrode 28 may be contracted to a width no greater than the maximum inside transverse dimension of the inner lumen 14, or preferably, to a width no greater than the maximum outside transverse dimension of the stylet head 27. The electrode portions 28a and 28b, and other electrodes discussed herein generally, can be spaced distally from an outer surface of the stylet head 27 by a distance of about 0.01 to about 0.05 inch, specifically about 0.02 to about 0.04 inch. The spacing of the bowed segments 48a and 48b can have similar spacing from the stylet head, but this spacing can vary significantly depending on the amount of radial inward contraction of electrode 28.

Figure 4D:
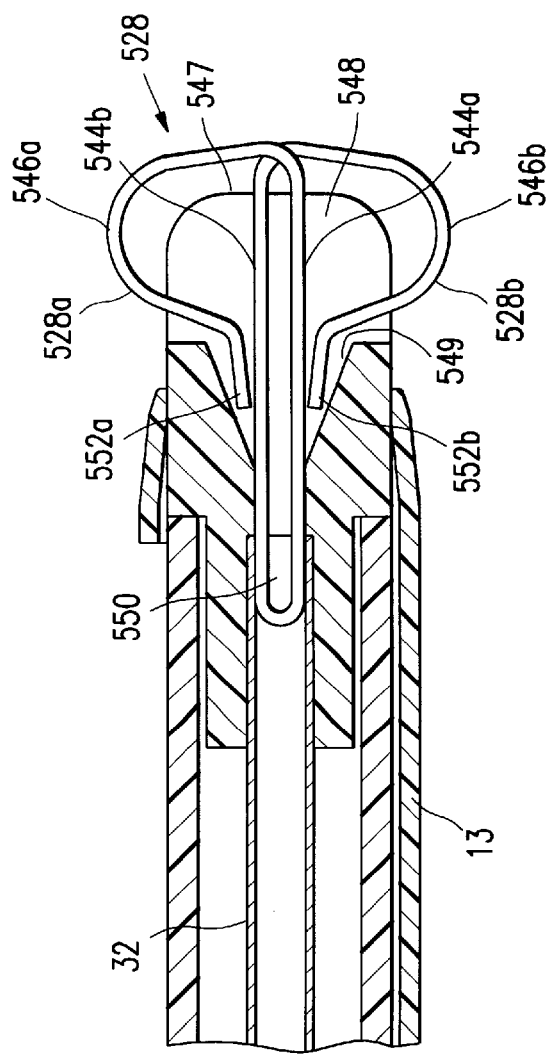

FIGS. 4A through 4E illustrate four additional embodiments of a stylet head and an electrode having features of the present invention. Referring first to FIG. 4A, electrode 128 comprises two electrode portions 128a, 128b. Each electrode portion 128a, 128b has a first or inner segment 144a, 144b, respectively, that extends axially through a central aperture 140 in the stylet head 126, and that is attached to and in electrical contact with the tubular central conductor 32. Each electrode portion 128a, 128b also has a second or outer segment 146a, 146b, respectively, that curves around the exterior of the stylet head 126, with a free end 147a, 147b that is received in a corresponding side opening 142 spaced proximally from the distal tip of the stylet head 126. The central aperture 140 in the tip of the stylet head 126 and/or the side openings 142 are dimensioned so that the electrode portions 128a, 128b may be deflected inwardly to the point that the maximum width of the electrode 128 is no greater than the maximum outside transverse dimension of the stylet head 126. In the embodiment illustrated, each of the side openings 142 extends into a slot 143 that is directed toward the distal tip of the stylet head 126. The slots 143 provide space so that the electrode portions 128a, 128b may be received within the maximum cross-sectional dimension of the stylet head 126. Alternatively, the maximum outside transverse dimension of the stylet head 126 may be sufficiently smaller than the maximum inside transverse dimension of the inner lumen 14 that there is space for the electrodes between the stylet head 126 and the inner surface of the cannula barrel 13.

In the embodiment illustrated in FIG. 4B, electrode 328 comprises a pair of opposed electrode portions 328a, 328b, each of which comprises an inner segment 344a, 344b, respectively, that is electrically connected to the tubular central conductor 32, and an outer loop segment 348a, 348b, respectively. Each of the outer loop segments 348A, 348b terminates in a free end 349a, 349b, respectively. A stylet head 326 includes a pair of diametrically-opposed side openings 342 and a central cavity 343 at its distal tip. Each of the loop segments 348a, 348b extends out from one of the side openings 342, curving around the exterior of the stylet head 326 toward its distal tip. The free ends 349a, 349b of the loop segments 348a, 348b are turned inwardly to extend substantially axially into the central cavity 343 in the distal tip of the stylet head 326. The cavity 343 is wide enough to allow the free ends 349a, 349b of the electrode loop segments 348a, 348b to move as the electrode portions 328a, 328b are deflected inward relative to the stylet head 326.

Referring next to the embodiment illustrated in FIG. 4C, electrode 428 is formed of a single wire loop, having a pair of ends 444 that are connected to the tubular central conductor 32. A stylet head 426 includes a pair of diametrically-opposed side recesses 442. The electrode 428 includes a pair of diametrically-opposed fingers 445 that are directed radially inwardly so as to be received in the side recesses 442 when the electrode 428 is contracted by being resiliently deflected inwardly.

Figure 4E:
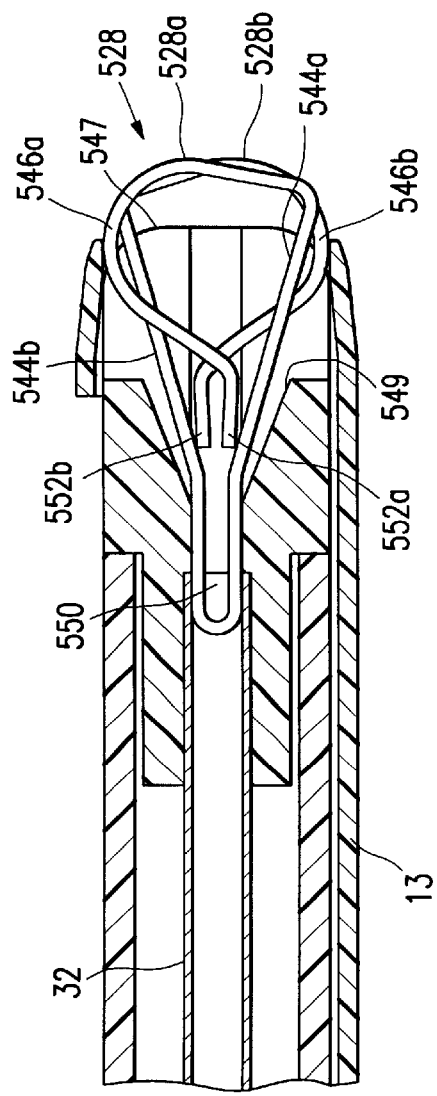

FIGS. 4D and 4E illustrate another embodiment of an electrode 528 having features of the present invention. FIG. 4D shows the electrode 528 in its expanded deployed configuration, while FIG. 4E shows the electrode in a contracted configuration. The electrode 528 is formed of two overlapping, opposed electrode portions 528a, 528b, each of which forms slightly over half the entire electrode width, with the two electrode portions 528a, 528b overlapping slightly in the middle when the electrode is in an expanded deployed configuration (FIG. 4D). The electrode portions 528a, 528b comprise, respectively, inner linear segments 544a, 544b and outer loop segments 546a, 546b. A stylet head 547 terminates in a slotted opening 548 through which the outer loop segments 528a, 528b extend when the electrode 528 is deployed. The slotted opening 548 communicates with a tapered central cavity 549 in the stylet head 547 that, in turn, communicates with an axial bore 550. The linear inner electrode segments 544a, 544b extend through the central cavity 549 and the axial bore 550, to the distal end of the tubular conductor 32, to which they are electrically connected. The outer loop segments 546a, 546b terminate in free ends 552a, 552b, respectively, that extend part way into the central cavity 549.

The outer loop segments 546a, 546b are each formed into a curve that extends beyond the outer diameter of the distal tip of the stylet head 547, so that in an expanded deployed position, illustrated in FIG. 4D, the maximum width of the electrode 528 (comprising the two electrode portions 528a, 528b) is greater than the maximum outside transverse dimension of the elongate shaft 26, and is at least as great as the maximum outside transverse dimension of the cannula barrel 13. In one embodiment of the invention, the maximum width of the electrode 528 is approximately 1.5 times the maximum outside transverse dimension of the cannula barrel 13. In another embodiment, the maximum width of the electrode 528 can be from about 2 to about 14 mm, specifically, about 4 to about 12 mm, and more specifically, about 7 to about 8 mm. The maximum width of embodiments of other electrodes discussed herein can have similar dimensions.

As shown in FIG. 4E, the slotted opening 548 at the distal tip of the stylet head 547 provides a recess into which the outer loop segments 546a, 546b of the electrode portions 528a, 528b, respectively, may be resiliently deflected. Inward radial force on either or both of the electrode portions 528a, 528b deflects them toward the center of the stylet head 547. The outer loop segment of each electrode portion fits into the slotted opening 548 when such inward pressure is applied, so that the primary electrode 528 may be contracted to a width no greater than the maximum inside transverse dimension of the inner lumen 14, or preferably, to a width no greater than the maximum outside transverse dimension of the stylet head 547. In this contracted configuration, the free ends 552a, 552b of the electrode portions 528a, 528b, respectively, cross over each other within the cavity 549.

Figure 5:
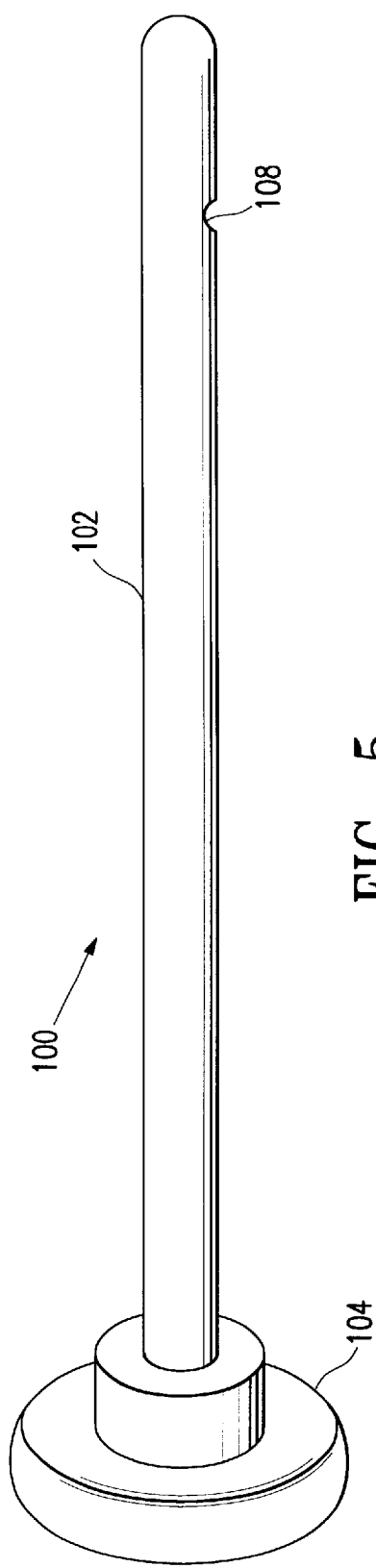
FIG. 5 is a perspective view of a guide tube having features of the present invention.
Figure 6:
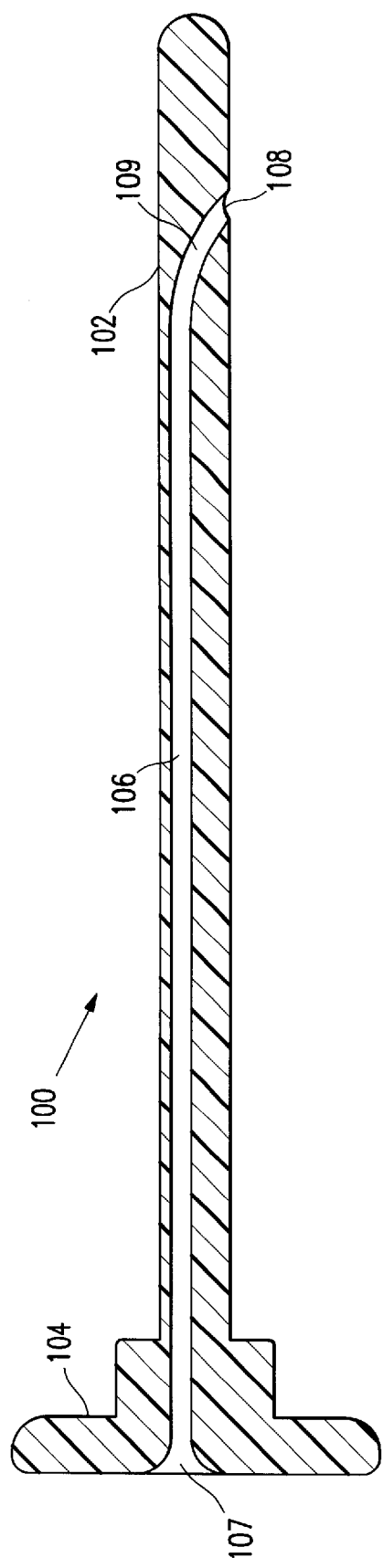
FIG. 6 is a longitudinal cross-sectional view of the guide tube illustrated in FIG. 5.

Referring to FIGS. 5 and 6, a guide tube 100 is illustrated that may be inserted into and through the inner lumen 14 for guiding other instruments for certain procedures. As noted above, the cannula 12, once inserted into the patient's tissue at the appropriate position, provides access to a desired site or a target tissue site under examination. The guide tube 100 provides a guide for instruments and other devices, so that further procedures may be performed in the region under examination. Use of the guide tube 100 can facilitate guiding instruments having external dimensions that are substantially less than the interior dimensions of the inner lumen 14.

The guide tube 100 includes an elongate shaft 102 with a flange 104 at the proximal end. The guide tube 100 may be formed of the same material as the cannula 12 and the stylet 24, or a similar material. Referring specifically to the elongate cross-sectional view of FIG. 6, a central bore 106 extends longitudinally along the length of the guide tube 100 from a proximal opening 107 at the proximal end of the guide tube 100. The guide tube bore 106 is not necessarily aligned with the axis of the guide tube 100. A short distance proximally from the distal end of the guide tube 100, the central bore 106 includes a radiused portion 109 where it bends radially to open through a side orifice 108. The side orifice 108 of the guide tube 100 is positioned along the length of the guide tube 100 so that when the guide tube 100 is inserted into the inner lumen 14, the guide tube side orifice 108 may be aligned with the cannula side aperture 16 (see FIG. 1). The radius of curvature of the radiused portion 109 of the central bore 106 is large relative to the transverse dimension of the guide tube, so that the bore 106 may easily guide the end of an instrument or other device inserted through it.

The central bore 106 of the guide tube 100 may also allow the guide tube 100 to serve as a secondary cannula, to provide a conduit or working channel for directing fluid, gel, paste or other semifluid material to the region of the patient's body adjacent the guide tube orifice 108. For example, a surgical dye may be injected through the bore 106 to mark the region and to provide a guide for subsequent surgical procedures. Also, hemostatic agents (such as those that contain fibrin or a fibrin/fibrinogen mixture) may be introduced through the guide tube bore 106 and the side orifice 108 to stem bleeding that may occur during a biopsy procedure.

In certain circumstances, it may be desired to provide a guide tube 100' having an orifice 110 at its distal tip, as shown in FIG. 7. The central bore (not shown) of the guide tube 100' of FIG. 7 could be substantially linear from the proximal opening to the distal orifice 110. FIG. 7 also shows the optional provision of a Luer fitting 112 connected to the proximal end of the guide tube 100' to facilitate the introduction of a fluid to the guide tube bore. A similar Luer fitting may be employed with the guide tube 100 of FIGS. 5 and 6.

FIG. 8 illustrates an exemplary electrocautery unit 150 that may be used to cauterize a biopsy cavity after removal of a tissue sample. The electrocautery unit 150 may be inserted through the bore of either of the guide tubes 100, 100' illustrated in FIGS. 5, 6, and 7, when the guide tube is installed in the cannula. The electrocautery unit 150 includes an elongate shaft 152 extending distally from a grip portion 154. The shaft 152 and the grip portion 154 enclose an electrical conductor (not shown) that extends proximally from the grip portion 154 to a power cable 156 that is connected to an electrical power source (not shown). The shaft 152 terminates in a distal end portion 158 on which is located an electrocautery element 160 that is electrically connected to the conductor.

The outside diameter of the shaft 152 of the electrocautery unit 150 is slightly less than the inside diameter of the central bore 106 of the guide tube 100. The distal end portion 158 of the electrocautery unit 150 is flexible, so that as the electrocautery unit 150 is inserted through the central bore 106 of the guide tube 100, the end portion 158 of the electrocautery unit 150 bends as it encounters the radiused portion 109 of the central bore 106 of the guide tube 100, and it may be guided out the guide tube side orifice 108.

FIG. 9 illustrates a biopsy marker insertion device 170 that may be inserted through the central bore of either of the guide tubes 100, 100' illustrated in FIGS. 5, 6, and 7. The biopsy marker insertion device 170 may be pre-loaded with a plurality of markers 172 that can be selectively dispensed through the side orifice 108 of the guide tube 100 when the guide tube is inserted through the cannula 12, and the side orifice 108 of the guide tube is aligned with the cannula side aperture 16. The markers 172 may be temporary markers made of a gelatin marker material, or they may be permanent markers, such as metal clips. Previously noted U.S. patent application Ser. No. 09/343,975 describes the use of such temporary and permanent markers, and its disclosure is incorporated herein by reference.

Figure 10:
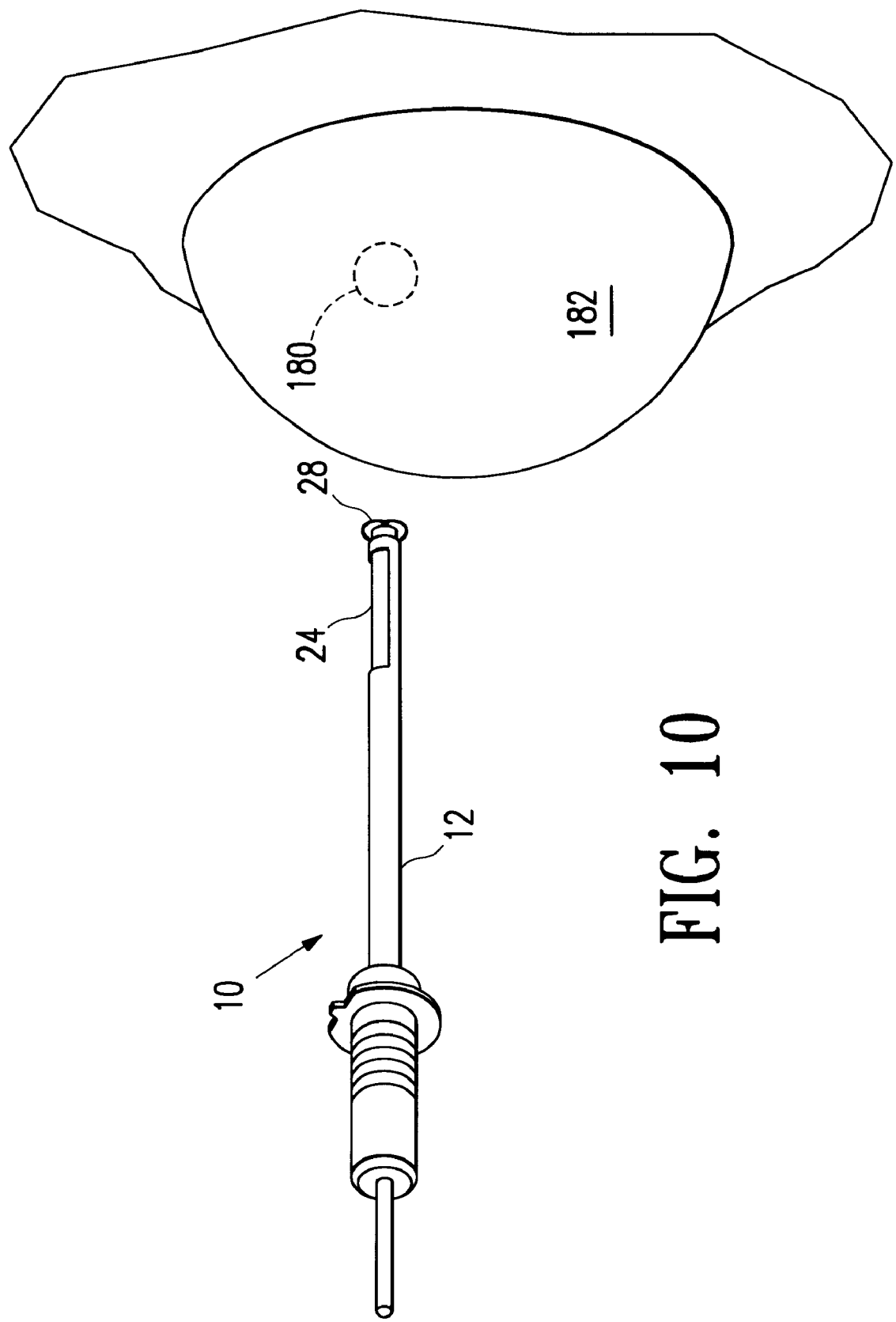
FIGS. 10 through 17 illustrate a biopsy procedure performed having features of the present invention, and using the system shown in FIGS. 1–4.

FIGS. 10 through 17 illustrate a method of taking a biopsy sample from a desired site or a target tissue site 180 (e.g., a suspected lesion or tumor) located within a human breast 182, having features of the present invention. Referring to FIG. 10, the system 10, comprising the cannula 12 and the electrosurgical stylet 24 with the electrode 28, is shown assembled and ready to pass into the breast tissue to the target site 180. Typically, an incision is first made (e.g., with a conventional scalpel) through the patient's skin. With the stylet 24 in its extended position, in which the electrode 28 is deployed, the distal end 27 of the stylet 24 is inserted into the incision. In accordance with the use of conventional electrosurgical apparatus, the operator activates an electrosurgical generator (not shown) using a control switch (not shown), such as a foot pedal, to apply high frequency electrical energy to the electrode 28 through the central electrical conductor 32 that extends along the length of the stylet 24. In one embodiment of the invention, the electrosurgical generator can operate about 500 to about 1000 KHz, specifically, about 700 to about 900 KHz. Power output for such an electrosurgical generator can be about 50 to about 150 watts, specifically, about 80 to about 100 watts. As the electrode 28 contacts the tissue, the tissue is ablated, allowing insertion of the stylet 24 and the surrounding cannula 12 through the tissue.

Figure 11:
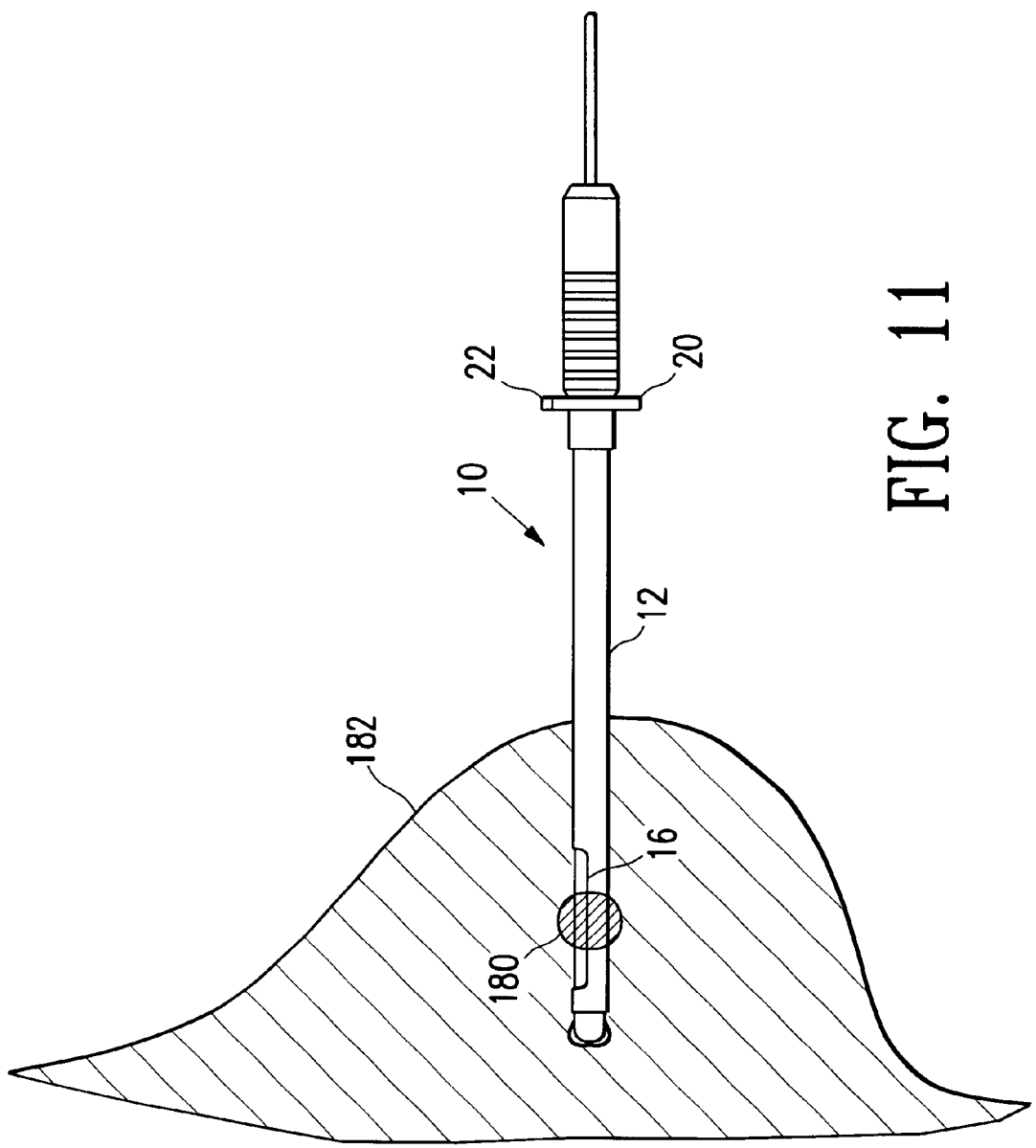

As described above, the electrode 28, in an expanded deployed state, can be wider than an outside transverse dimension of the cannula 12, so that the electrode 28 makes a passage through the tissue sufficiently large to permit the cannula 12 to be readily inserted. The electrosurgical ablation process is continued until the system 10 is appropriately positioned with regard to the target site 180, e.g., to the point that the target site 180 and the cannula side aperture 16 coincide, as shown in FIG. 11.

Once the cannula 12 is in place, with the cannula side aperture 16 providing access to the target site 180, the stylet 24 is removed, leaving the cannula 12 in place. The orientation point 22 on the cannula flange 20 identifies the orientation of the cannula aperture 16, so that the cannula 12 provides a guide for the subsequent insertion of other instruments and devices for removing samples of the suspected tumor or lesion at the target site 180, and for performing other procedures.

As the stylet 24 is withdrawn from the cannula 12, the electrode 28 is resiliently deflected or contracted, as described above, so that the stylet 24 may be easily removed from the cannula 12. Referring particularly to the embodiment illustrated in FIGS. 3 and 4, as the stylet 24 is removed, the distal end of the cannula barrel 13 applies inward pressure on the bowed segments 48a, 48b of the two electrode portions 28a, 28b, pressing the electrode portions 28a, 28b toward each other, until the electrode portions 28a, 28b are contained in the slots 42 in the stylet head 27. One of the electrode portions (e.g., the electrode portion 28a) may be aligned with the cannula side aperture 16, and thus may return to its deployed position as the stylet head 27 passes by the cannula side aperture 16. However, as the stylet head 27 continues along the length of the cannula barrel 13, the wall of the cannula barrel 13 again applies pressure to the electrode portions 28a, 28b, flexing the electrode portions 28a, 28b toward each other again, so that the stylet 24 may continue to be withdrawn from the cannula 12.

Figure 12:
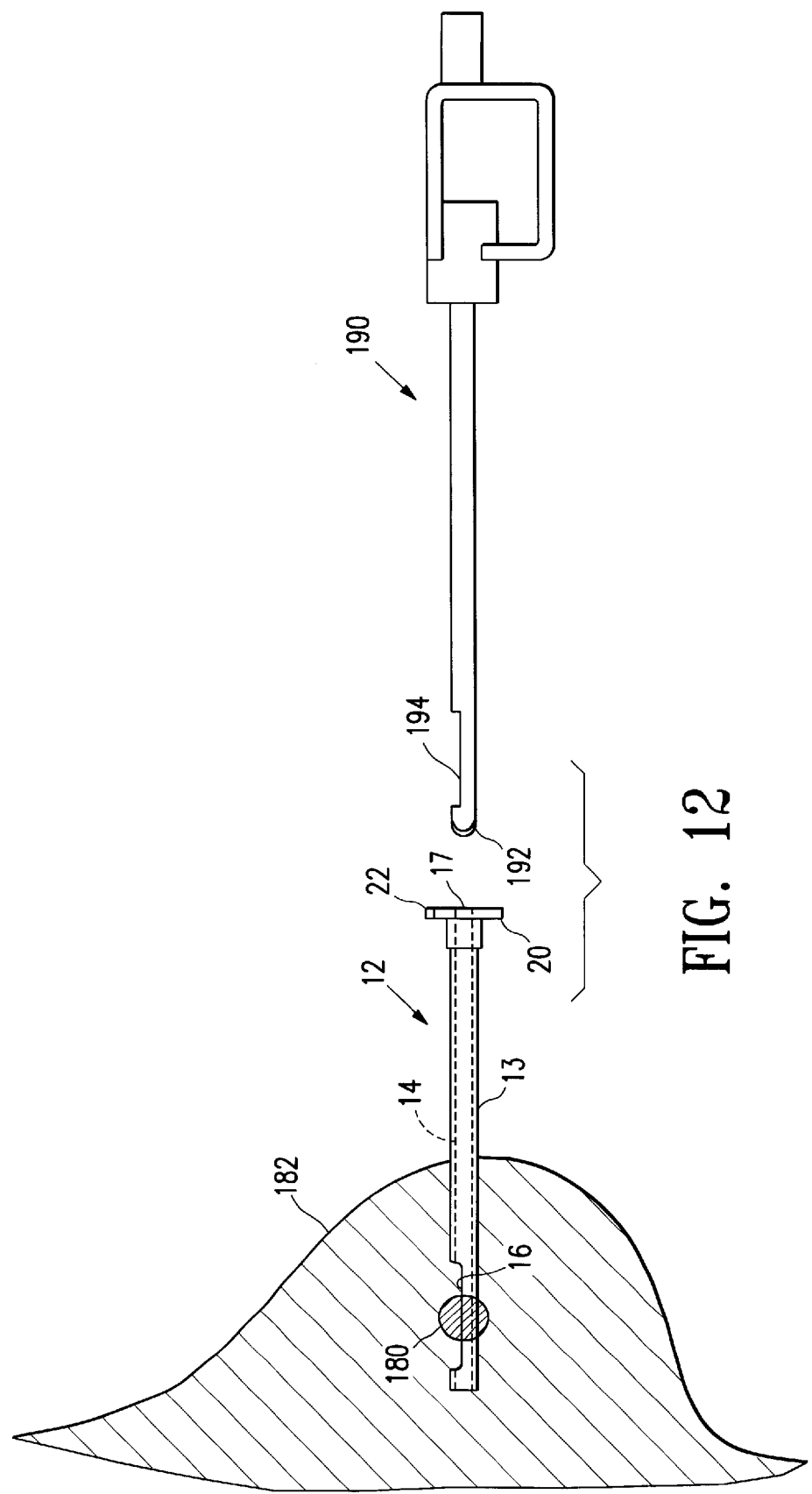
Figure 13:
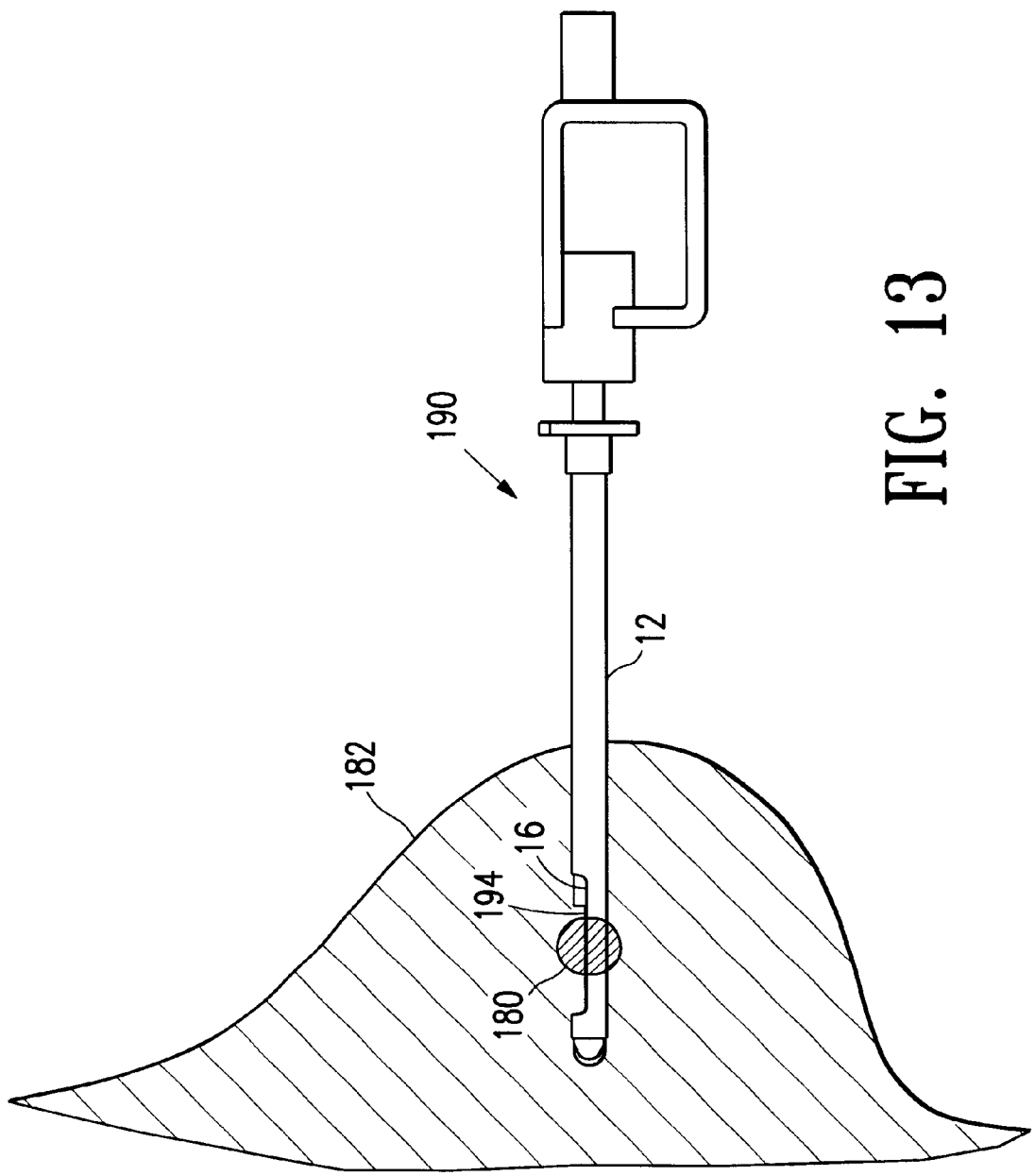

Referring next to FIGS. 12 and 13, a biopsy device 190 is inserted through the cannula 12 to take a tissue sample from the target site 180. The biopsy device 190 is advantageously of the type described in U.S. Pat. Nos. 5,526,822; 5,649,547; 5,775,333; and 5,928,164, the disclosures of which are incorporated herein by reference. The biopsy device 190 includes a cutting edge 192, such as a knife edge or an electrosurgical electrode element, at its distal end. A sample chamber 194 is provided to hold the biopsy sample. When the biopsy device 190 is used with the present invention, the cutting edge 192 of the biopsy device 190 is generally not necessary for creating the incision to access the target site 180.

The biopsy device 190 is inserted into the proximal cannula opening 17 and through the inner lumen 14 of the cannula 12, as shown in FIGS. 12 and 13, until the sample chamber 194 of the biopsy device is aligned with the cannula side aperture 16. A portion of the tissue at the target site 180 tends to fill the sample chamber 194 of the biopsy device 190 when the biopsy device 190 is thus positioned. The biopsy device 190 has a second cutting edge (not shown) at the distal end of the sample chamber 194 that severs the tissue captured in the sample chamber 194 from the surrounding tissue. The biopsy device 190 is then withdrawn from the cannula 12 with a biopsy sample contained within the sample chamber 194, leaving a biopsy cavity in the tissue surrounding the target site 180.

In many instances it is desirable to take multiple samples from the target site 180. To take multiple samples, the cannula 12 may be rotated, so that samples at different orientations may be taken. The orientation notch 22 on the cannula flange 20, which remains external to the patient, provides the operator with a direct physical visual indication of the location of the cannula side aperture 16 through which the sample is being taken. Some biopsy devices permit multiple samples to be withdrawn with a single insertion of the biopsy device. Otherwise, the biopsy device 190 may be used to remove one sample at a time through the cannula 12, which remains in place.

Figure 14:
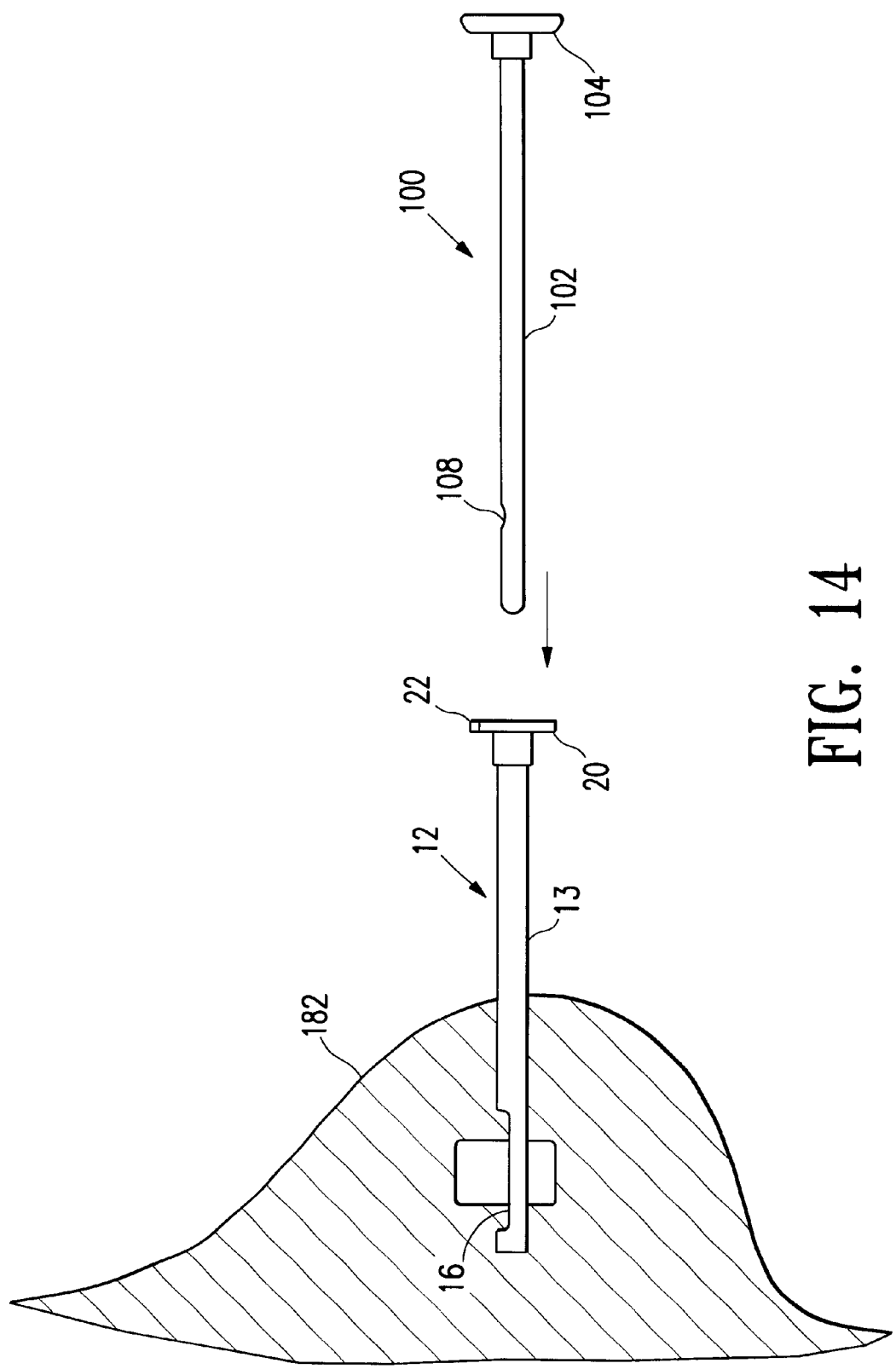

After the desired number of biopsy samples are removed, the biopsy device 190 may be removed from the cannula 12, and the guide tube 100 inserted, as shown in FIG. 14. The operator slides the guide tube 100 into the cannula 12 until the guide tube orifice 108 is aligned with the cannula side aperture 16. Preferably, the guide tube 100 is constructed so that when the guide tube flange 104 abuts or nearly abuts the cannula flange 20, the guide tube orifice 108 is properly positioned in longitudinal alignment with the cannula aperture 16. A marker (not shown) on the guide tube flange 104 may indicate the rotational orientation of the guide tube 100, so that the guide tube orifice 108 maybe rotationally aligned with the cannula aperture 16, as indicated by the orientation point 22 on the cannula flange 20.

Figure 15:
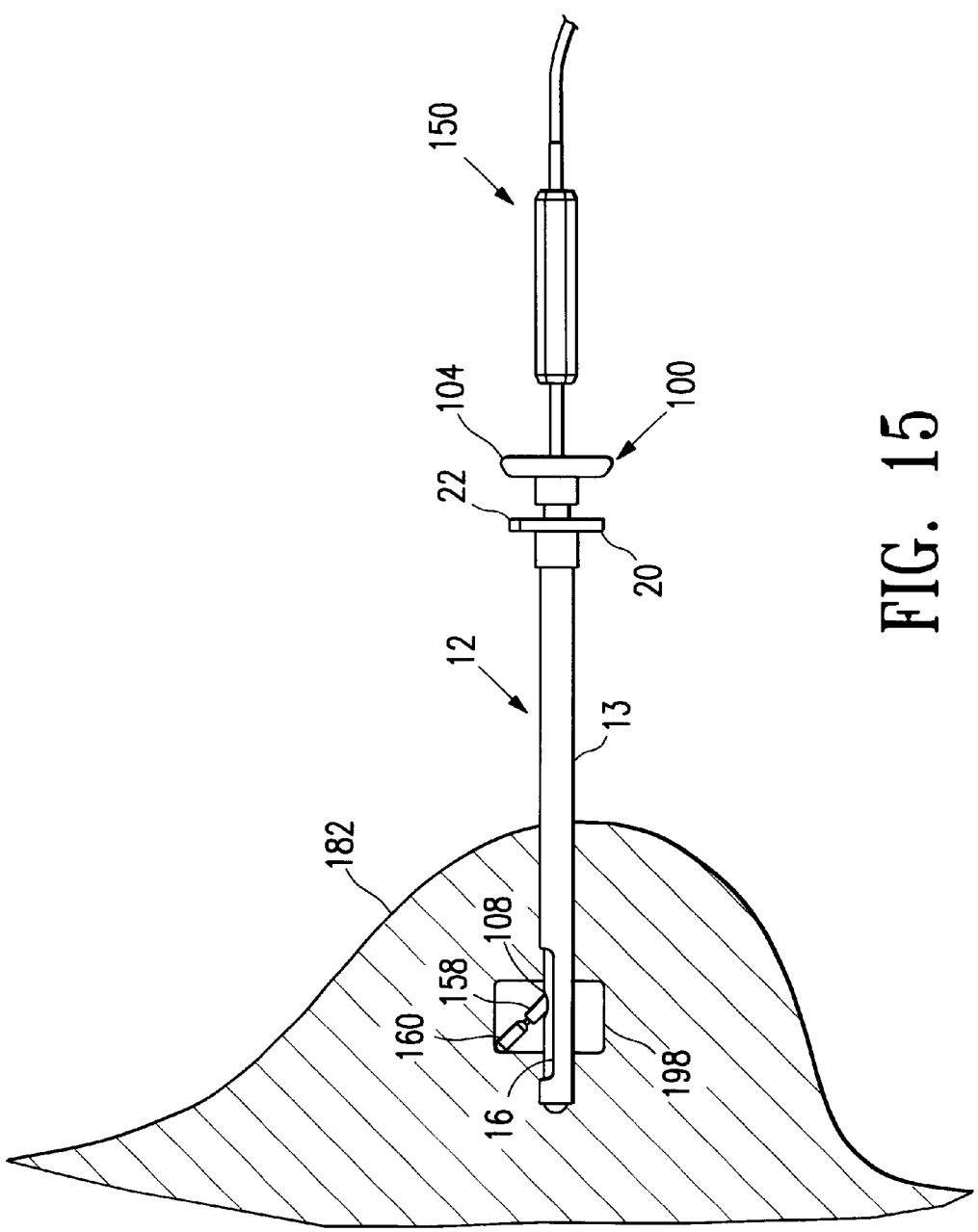

A cauterization device, such as the electrocautery unit 150 illustrated in FIG. 8, may be inserted, as shown in FIG. 15, through the guide tube 100 until the electrocautery element 160 protrudes from the guide tube orifice 108 into a cavity 198 remaining after the removal of the biopsy sample or samples. The operator activates the electrocautery unit 150 to cauterize the region from which the samples were taken, to stop bleeding and reduce the probability of infection. The cannula 12 may be rotated to allow the electrocautery unit 150 to access all areas of the biopsy cavity 198.

Following cauterization, the electrocautery unit 150 is removed from the guide tube 100, leaving the guide tube 100 and cannula 12 in place. As noted above, it is often desirable to place markers to identify the location from which the samples were taken. If tests on the sample indicate that surgery is called for to remove the target tissue site 180, the markers identify the location of the target site 180 using x-rays, ultrasound, or other imaging techniques, to permit the surgeon to remove the appropriate tissue. In some instances, it may be desirable to mark the location from which the biopsy samples were taken with a permanent marker. This may be appropriate when the examination determines that the target tissue site 180 is benign. Doctors may find it helpful to identify in subsequent examinations of the patient that the suspect tissue mass has previously been examined, and determined not to require further biopsy. Location markers for such purposes are typically permanent, but they may alternatively be temporary, designed to be absorbed into the body in a few weeks to a few months. Permanent markers may include metal clips that are visible with x-rays. Temporary markers may be formed of a biocompatible, radiopaque gel that is absorbed over time in the body tissue. Both temporary and permanent markers are described in previously noted U.S. patent application Ser. No. 09/343,975, filed Jun. 30, 1999.

Figure 16:
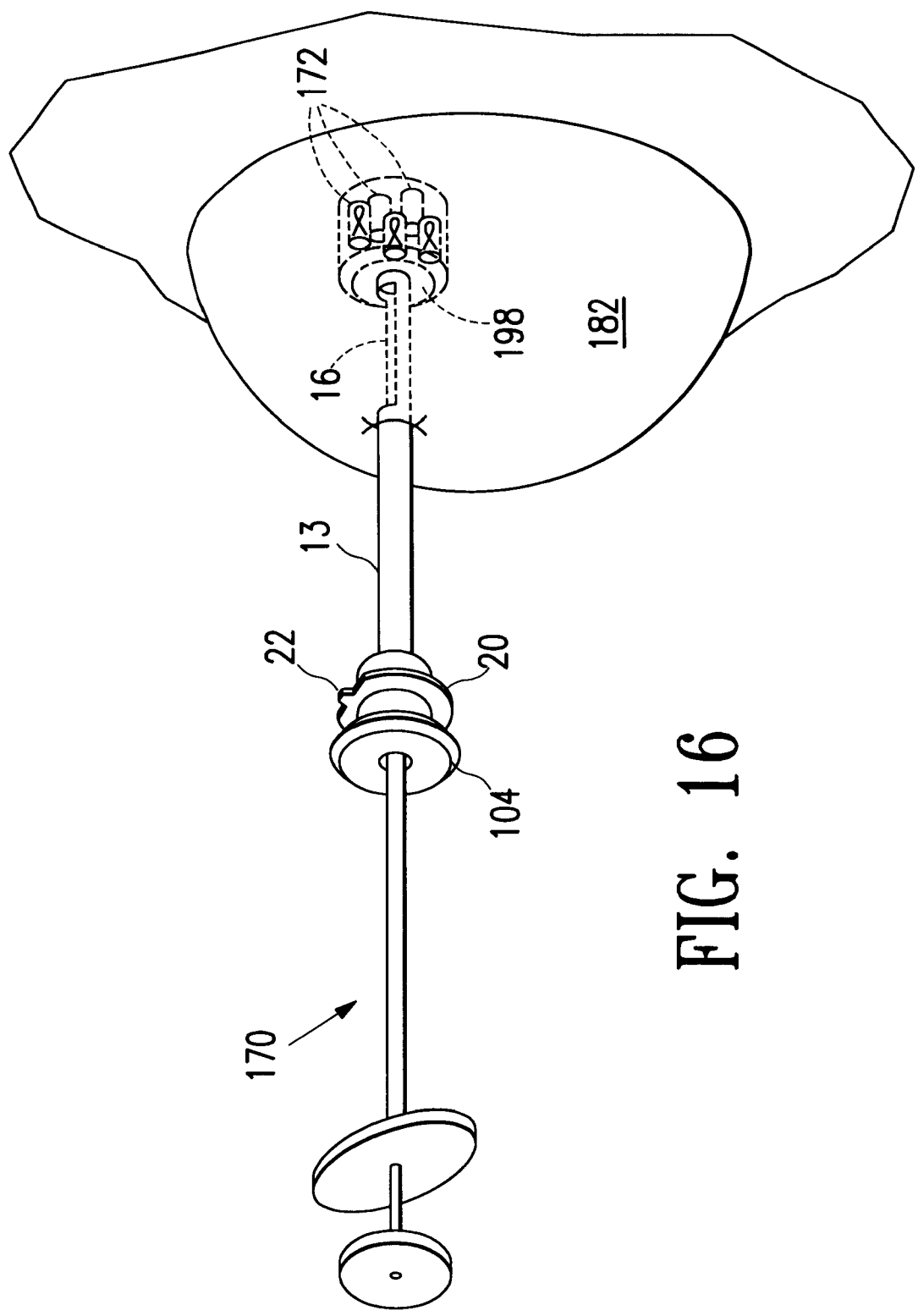
Figure 17:
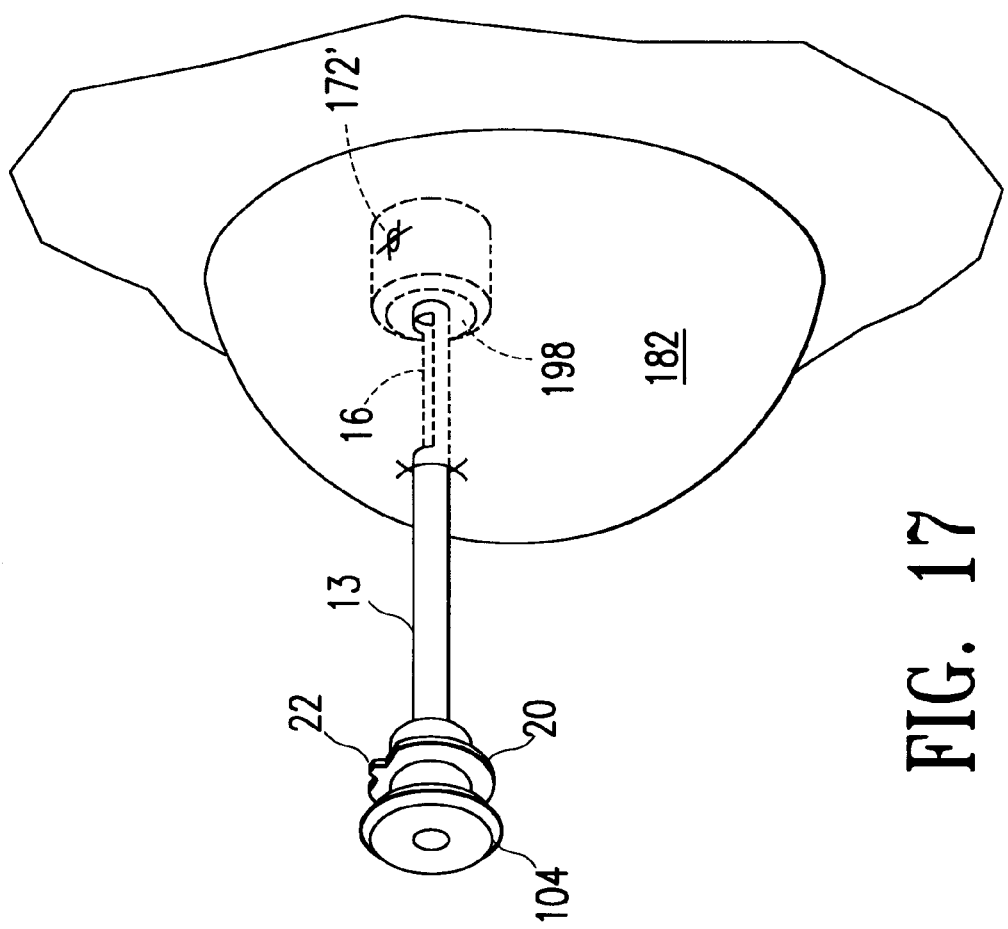

A marker insertion device for placing such markers may be guided through the guide tube 100 installed in the cannula 12. For example, the marker installation device 170 described above and shown in FIG. 9 may be inserted through the central bore 106 of the guide tube 100. As the distal end of the marker insertion device emerges from the guide tube orifice 108 (which is aligned with the cannula aperture 16), the marker elements 172 may be dispensed into the biopsy cavity 198. FIG. 16 illustrates the marker installation device 170 partially removed from the guide tube 100, after placing several temporary markers 172 in the biopsy cavity 198. Similarly, the marker installation device 170 (or one closely similar to it) may be used to install a permanent marker, such as a metal clip 172, as shown in FIG. 17.

Other devices or materials may be inserted into the biopsy cavity 198 using the cannula/guide tube combination. For example, a surgical dye and/or a hemostatic agent may be injected, as discussed above.

At the conclusion of all procedures requiring access to the target tissue site 180 and the tissue surrounding it, the guide tube 100 and the cannula 12 may be removed from the patient's tissue. The incision formed by the initial electrosurgical cutting by the stylet 24 is then appropriately closed.

Figure 18:
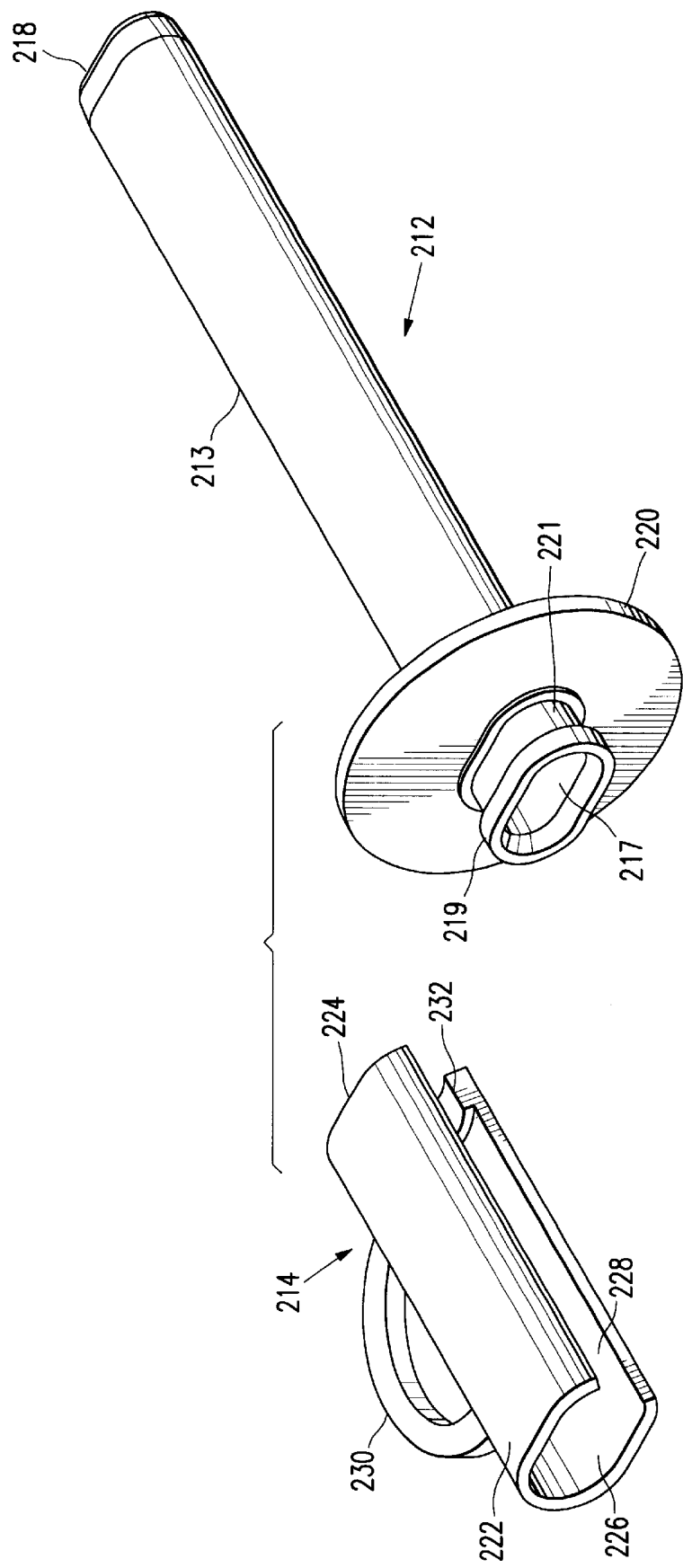
FIG. 18 is a perspective view of an embodiment of a cannula and a tubular spacer element having features of the present invention.

FIG. 18 illustrates an embodiment of a cannula 212 and a spacer element 214 having features of the invention. This embodiment may be employed in situations in which the invention is used in conjunction with cutting implements that have different configurations of cutting tips and apertures. Also, it may be employed in situations where the surgeon using the device, for a variety of reasons, does not wish to use a cannula with a side aperture.

Specifically, cannula 212 is similar to cannula 12 described above, except that it is shorter, and it lacks the side aperture 16. Thus, it comprises a tubular barrel 213 that is fully closed between an open proximal end 217 and an open distal end 218, and that defines a inner lumen between the proximal end 217 and the distal end 218. Surrounding the open proximal end 217 is an annular rim 219. An annular flange 220 surrounds the barrel 213 a short distance distally from the rim 219, thereby defining a circumferential spacer seat 221 between the rim 219 and the flange 220.

The spacer element 214 is designed to be removably attachable to the modified cannula 212. Specifically, the spacer element comprises a hollow, tubular body 222 having an open distal end 224 and an open proximal end 226, with a longitudinal slit or gap 228 from end to end. The body 222 is made of a flexible, resilient plastic. A gripping tab 230 is fixed to the body 222 diametrically opposite the slit 228. The tab 230 is preferably formed as a unit with the body 222 so as to be integral therewith. The body 222 is formed with an internal arcuate lip 232 adjacent the distal end 224.

Except for the arcuate lip 232, the inside diameter of the spacer element 214 is approximately the same as the outside diameter of the cannula rim 219. The lip 232 is dimensioned and configured to seat in the spacer seat 221 of the modified cannula 212. Thus, the spacer element 214 can be installed on the proximal end of cannula 212 by fining the cannula rim 219 into the spacer element body 222 through the slit 228, with the internal lip 232 of the body seated in the spacer seat 221 of the cannula 212. When the spacer element 214 is so installed, its distal end 224 abuts against the proximal side of the cannula flange 220, while its proximal end 226 extends some distance proximally from the proximal end 217 of the modified cannula 212. The spacer element 214 is thus resiliently held in engagement with cannula 212 until it is removed by pulling it to free the cannula 212 through the slit 228.

Figure 19:
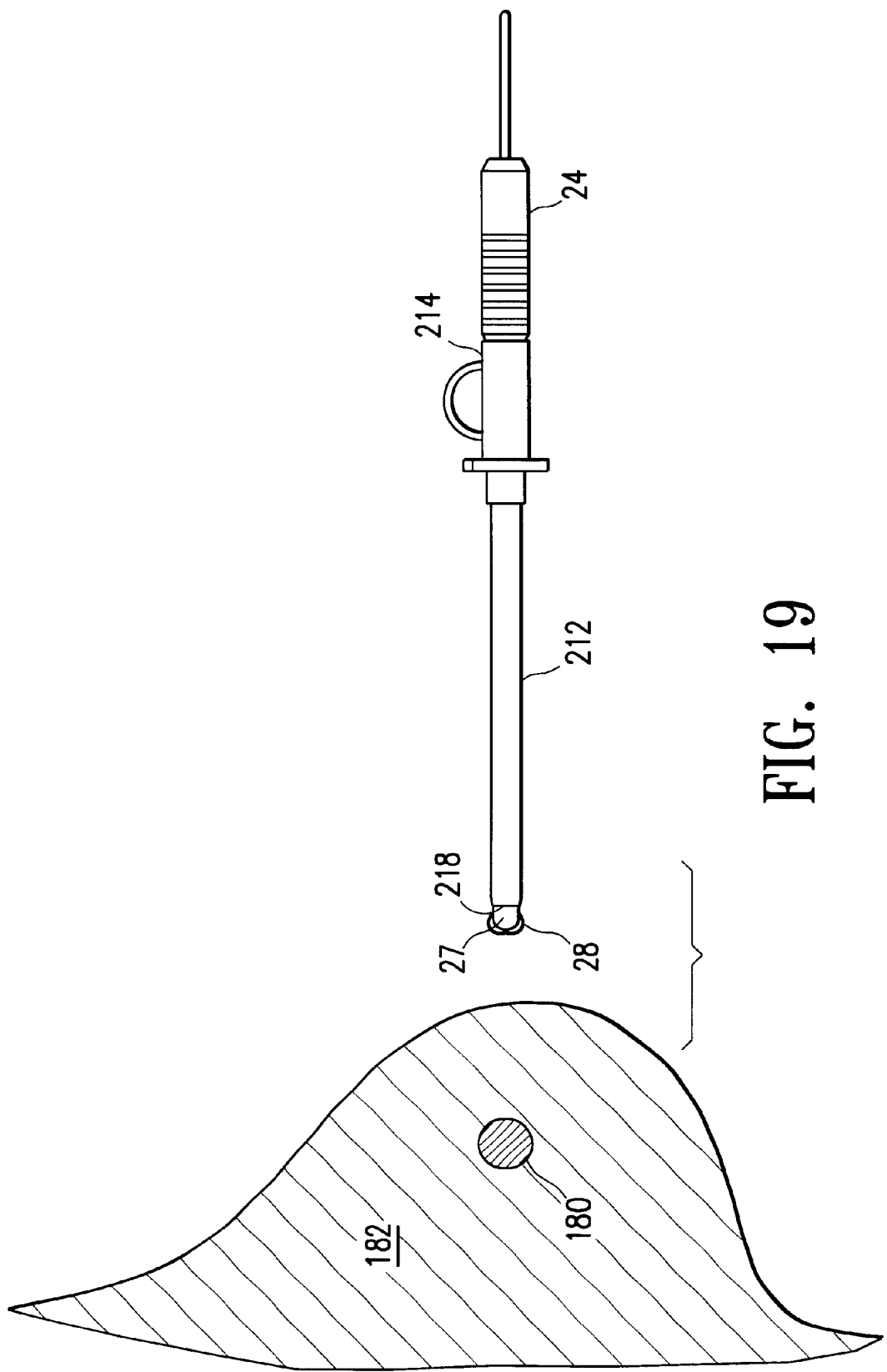
FIGS. 19 through 23 illustrate a biopsy procedure having features of the present invention, and using the cannula and tubular spacer element shown in FIG. 18.
Figure 20:
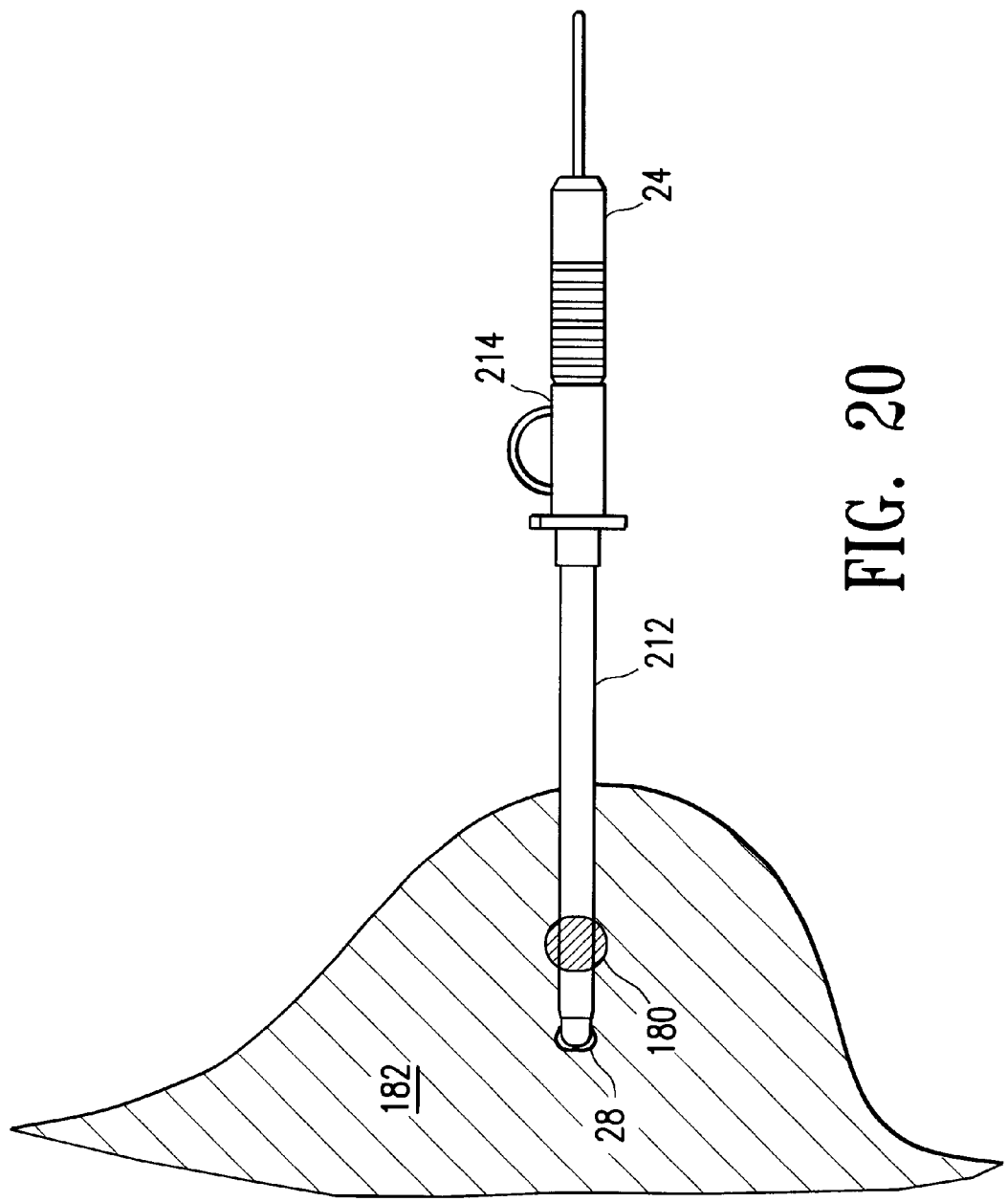
Figure 21:
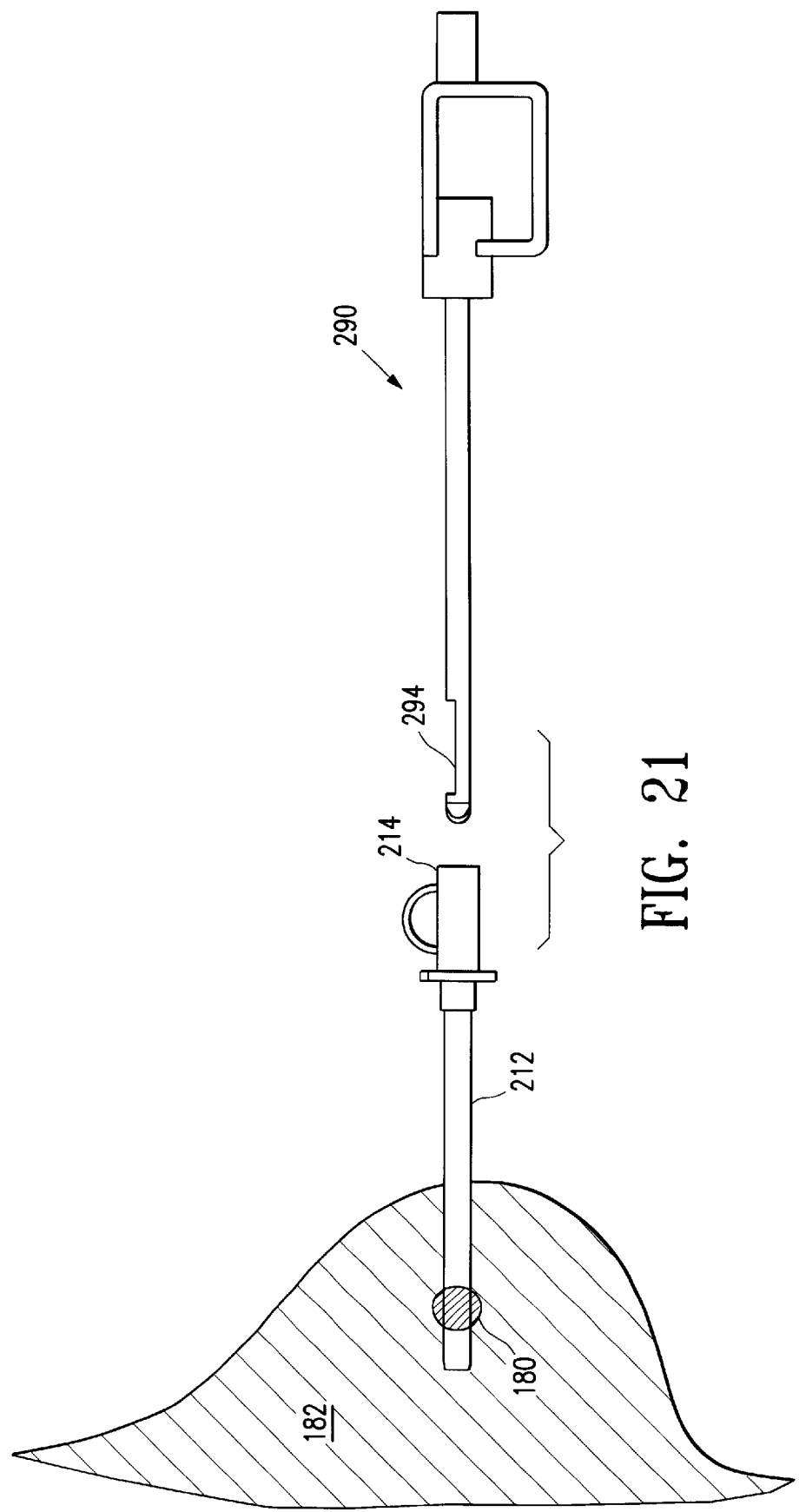
Figure 22:
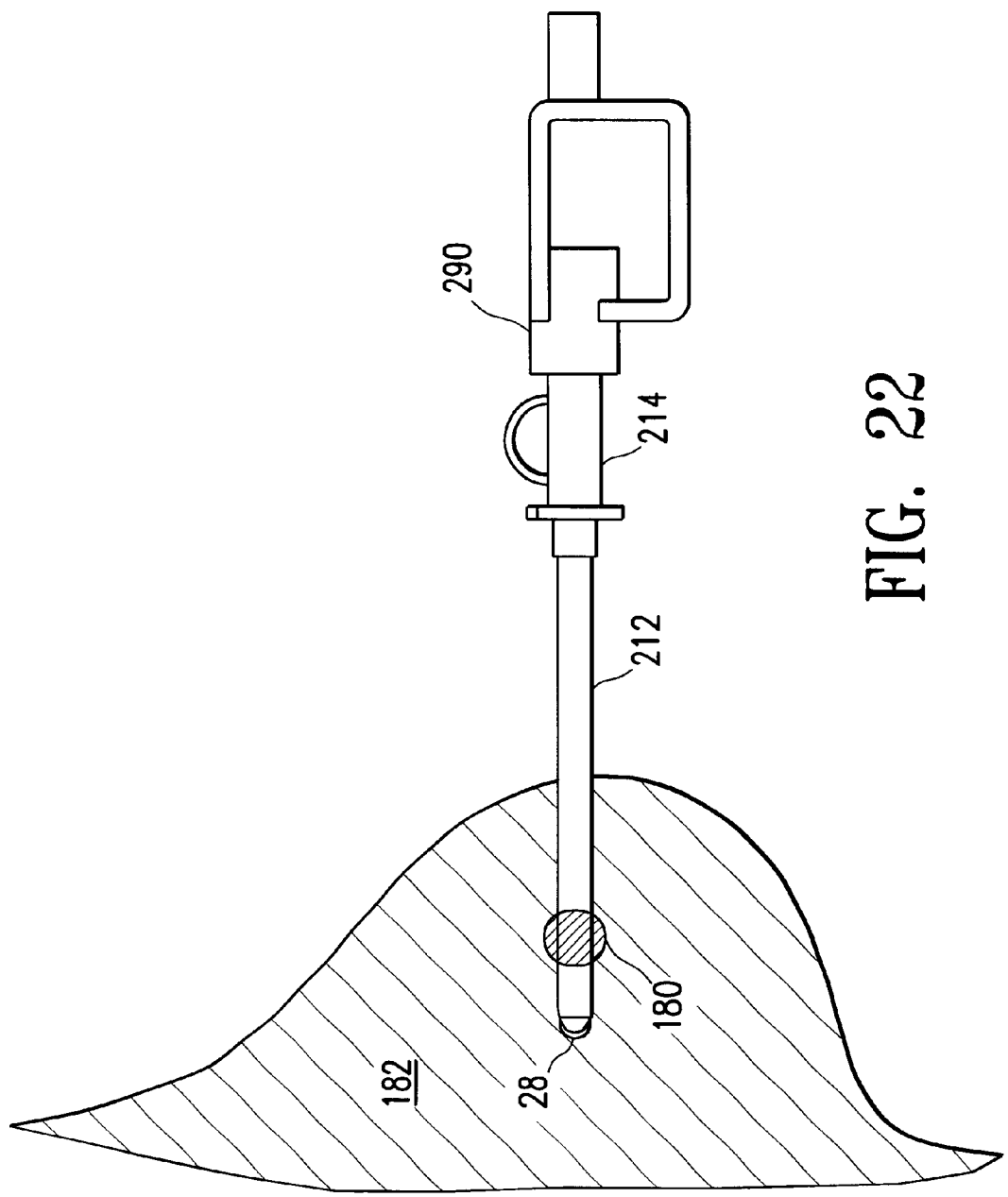
Figure 23:
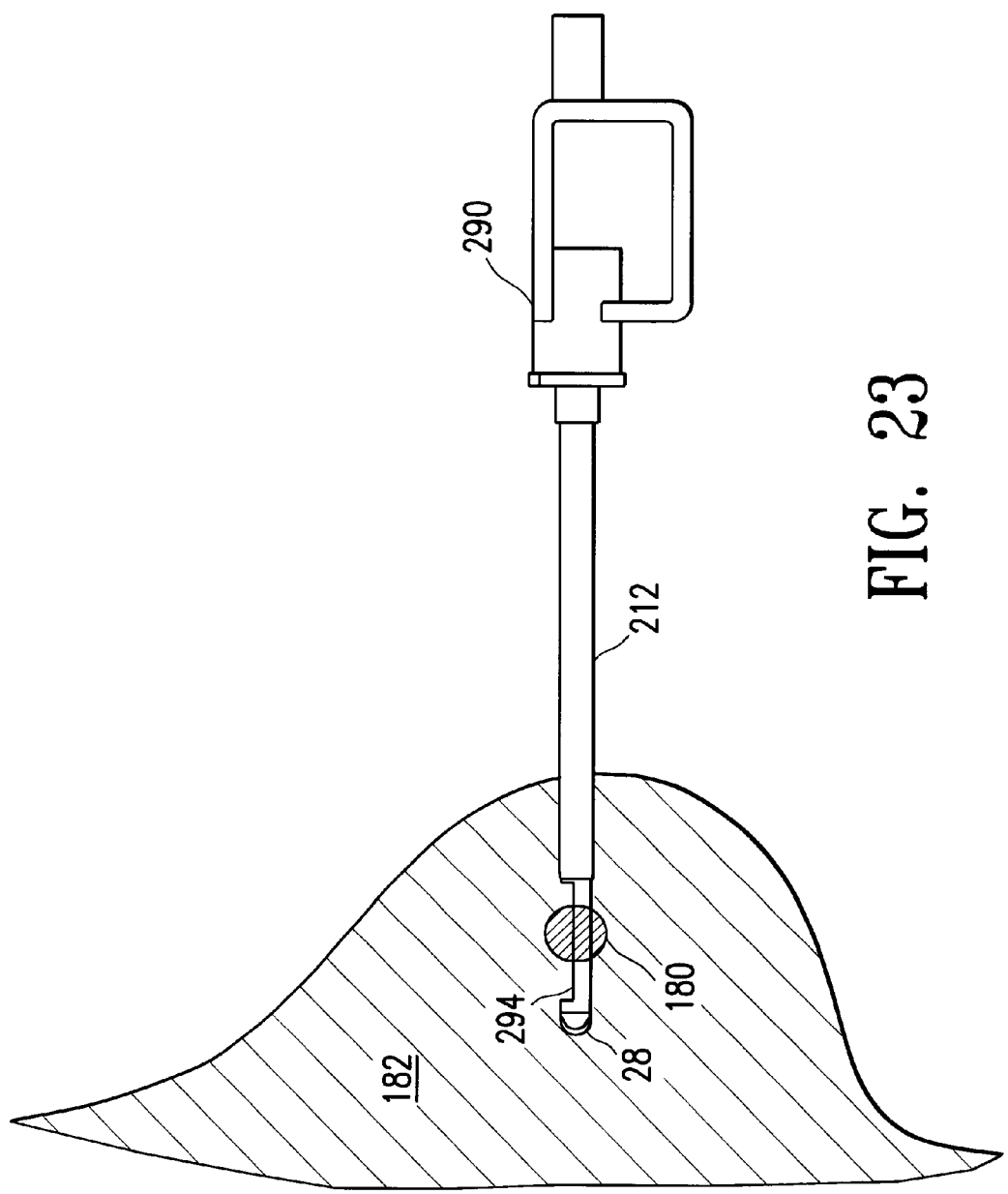

FIGS. 19–23 illustrate a method of using a system which includes cannula 212 and the spacer element 214 of FIG. 18. First, as shown in FIG. 19, the spacer element 214 is installed onto the proximal end of cannula. 212, as described above, and the stylet 24 of the invention is inserted through the spacer element 214 and cannula 212 to its deployed position, with electrode 28 exposed through the distal end 218 of the cannula 212. Then, as shown in FIG. 20, the electrode 28 is energized and the stylet 24 (with cannula 212) is advanced into the patient's body (e.g., the breast tissue 182) until the stylet head 27 passes through the target tissue mass 180. The stylet 24 is then withdrawn from the cannula. 212, but the spacer element 214 is left attached to the proximal end of the cannula 212, as shown in FIG. 21. A biopsy device 290 (such as a mammotome), having a sampling chamber 294, is inserted into the cannula 212, as shown in FIGS. 21 and 22, so that the sampling chamber 294 is aligned with the target tissue mass 180. Finally, as shown in FIG. 23, the spacer element 214 is removed by pulling it off the cannula 212 using the gripping tab 230, and the cannula 212 is withdrawn proximally along the biopsy device 290, until the sampling chamber 294 of the biopsy device 290 is exposed within the target tissue mass 180. From this point, the biopsy sample is taken as described above in connection with FIGS. 12 and 13.

Those skilled in the art will recognize that various modifications may be made to the specific embodiments illustrated above without departing from the spirit of the present invention. For example, numerous modifications may be made to the shape of the electrosurgical deflecting primary electrode on the electrosurgical stylet, the shape of the cannula and instruments inserted through the cannula, including the guide tube, the electrocautery device, and the marker insertion device. In addition, it win be readily appreciated that other types of instruments may be inserted through the cannula in addition to or in place of the instruments described above. Furthermore, it will be recognized that additional steps may be added to the procedure described above, and that certain steps may be removed from the procedure in certain instances, depending on the specific needs of the patient. These and other modifications that may suggest themselves are considered to be within the spirit and scope of the invention, as defined in the claims that follow.

What is claimed is:

1. A system for accessing tissue at a desired site within a patient's body having a stylet which comprises:
    an elongate shaft with an outside transverse dimension, a proximal end, a distal end, and
    an electrosurgical electrode disposed at the distal end of the elongate shaft having a plurality of separately expandable arcuate electrode portions and having an expanded deployed configuration with a width greater than the outside transverse dimension of the elongate shaft and a contracted configuration having a width that is less than the width of the expanded deployed configuration.

2. The system of claim 1 further comprising a cannula having a proximal end, a distal end, proximal and distal opening and an inner lumen which extends between the proximal and distal openings wherein the stylet is dimensioned to be slidably received in the inner lumen of the cannula.

3. The system of claim 2 wherein the electrosurgical electrode has an expanded deployed configuration with a width greater than an outside transverse dimension of the cannula and a contracted configuration with a width that is not greater than an inside transverse dimension of the inner lumen of the cannula.

4. The system of claim 2, wherein the cannula includes a longitudinally extending side opening.

5. The system of claim 2, further comprising a guide tube which is slidably disposed within the inner lumen of the cannula, which has a proximal opening and an elongated distal side opening and which has a central bore extending between a proximal opening and the elongated distal side opening of the guide tube, the guide tube being positionable within the inner lumen of the cannula so that the guide tube distal side opening communicates with the distal side opening of the cannula.

6. The system of claim 1, wherein the electrode comprises at least one arcuate cutting element which is spaced distally of the distal end of the elongate shaft and which lies in a plane that is substantially parallel to a longitudinal axis of the elongate shaft.

7. The system of claim 1, wherein the electrode comprises first and second electrode portions that are resiliently deflectable in an inward radial direction when the electrode is constricted from the expanded deployed configuration to the contracted configuration.

8. The system of claim 1, further comprising a tubular spacer element which has a proximal end and a distal end and which is configured to be removably disposed about a proximal section of the elongate shaft and removably secured to the proximal end of the cannula.

9. The system of claim 1 wherein the stylet is configured to extend distally beyond the distal opening of the cannula when disposed within the inner lumen of the cannula.

10. The system of claim 2 wherein the width of the electrosurgical electrode in the expanded deployed configuration is substantially equal to one half the circumference of the distal end of the cannula.

11. The system of claim 2 further comprising a hand grip disposed on the proximal end of the stylet, a peripheral flange disposed on the proximal end of the cannula distal to the handle, and a locking lever disposed on the hand grip which detachably engages a notch on the peripheral flange.

12. The system of claim 11 further comprising a rotational position indicator disposed on the peripheral flange of the cannula which indicates the rotational position of the elongated distal side opening of the cannula.

13. A method of accessing tissue at a desired site within a patient's body, comprising:
    (a) providing the system of claim 2:
    (b) with the stylet disposed within the inner lumen and the electrode extending distally from the distal opening of the cannula in the expanded deployed configuration, energizing the electrode with high frequency electrical energy and advancing the system into the patient's body until the distal end of the stylet has been advanced at least partially into tissue at a desired site within the patient's body; and
    (c) withdrawing the stylet in a proximal direction while leaving the cannula within the patient's body.

14. The method of claim 13, wherein the cannula includes a longitudinally extending side aperture communicating with the inner lumen and the system is advanced and positioned so that the side aperture is disposed adjacent tissue at the desired site.

15. The method of claim 14, further comprising:
    (d) providing a guide tube dimensioned to be slidably received in the inner lumen of the cannula and having a central bore terminating in a side orifice; and
    (e) positioning the guide tube in the inner lumen so that the side orifice of the guide tube communicates with the side aperture of the cannula.

16. The method of claim 15, wherein the central bore and the side orifice of the guide tube are dimensioned to receive a selected surgical instrument.

17. The method of claim 13, wherein removing the stylet from the inner lumen includes resiliently deforming the electrode from the expanded deployed configuration to the contracted configuration.

18. A method of performing a biopsy at a desired site in a patient's body, comprising:
    (a) providing a system comprising:
        (i) a cannula having a proximal end, a distal end, an inner lumen having an inside transverse dimension and extending between proximal and distal openings, an outside transverse dimension and a longitudinally extending side aperture in fluid communication with the inner lumen, and
        (ii) a stylet which comprises
            an elongate shaft which has a proximal end, and a distal end, and which is dimensioned to be slidably received in the inner lumen of the cannula with the distal end of the elongate shaft extending distally from the distal opening of the cannula in an extended position, and
            an electrosurgical electrode disposed at the distal end of the elongate shaft having an expanded deployed configuration with a width greater than an outside transverse dimension of the cannula when the elongate shaft is in an extended position with the electrode extending distally from the distal opening of the cannula and a contracted configuration having a width that is not greater than an inside transverse dimension of the inner lumen when the electrode is disposed within the inner lumen;
    (b) providing a method of performing a biopsy at a desired site in a patient's body with said system having the stylet disposed in the inner lumen and the elongate shaft in its extended position, the method steps comprising: energizing the electrode and advancing the system into the patients body until the side aperture is located adjacent tissue at a desired site;
    (c) withdrawing the stylet from the inner lumen while leaving the cannula within the patient's body;
    (d) inserting a biopsy device through the inner lumen of the cannula to the side aperture of the cannula; and
    (e) obtaining a biopsy sample from the tissue at the desired site through the side aperture of the cannula.

19. The method of claim 18, further comprising:
    (f) withdrawing the biopsy device from the cannula passage while leaving the cannula in place in the patient's body.

20. The method of claim 18, further comprising:
    (f) withdrawing the biopsy device and the cannula from the patients body.

21. The method of claim 19, further comprising:
    (g) providing a guide tube dimensioned to be slidably received in the cannula passage and having a central bore terminating in a side orifice; and
    (h) positioning the guide tube in the cannula passage so that the side orifice of the guide tube communicates with the side aperture of the cannula.

22. The method of claim 21, further comprising:
    (i) providing an electrocautery device dimensioned to be received in the central bore of the guide tube and having a distal end with a cauterizing element, the distal end being configured to be extendable through the side orifice of the guide tube;

(j) inserting the electrocautery device through the central bore of the guide tube so that the cauterizing element extends through the side orifice of the guide tube into tissue adjacent the side orifice; and (k) cauterizing the tissue adjacent the side orifice.

23. The method of claim 22, further comprising:

(l) providing a surgical marker installation device dimensioned to be received in the central bore of the guide tube and having a distal end configured to be extendable through the side orifice of the guide tube;

(m) inserting the surgical marker installation device through the central bore of the guide tube so that the distal end extends through the side orifice of the guide tube into tissue adjacent the side orifice; and (n) installing a surgical marker in the tissue adjacent the side orifice.

24. A system for accessing a subcutaneous tissue site in a patient's body, comprising:

a cannula having an inner lumen disposed between and in fluid communication with proximal and distal openings, the inner lumen having an inside transverse dimension and the cannula having an outside transverse dimension;

a longitudinally extending side aperture in the cannula near the distal opening and communicating with the inner lumen;

a biopsy device assembly dimensioned to be selectively received within the inner lumen and to be axially movable therein, having a stylet dimensioned to be slidably received in the inner lumen, terminating in a distal end at which is located an electrosurgical electrode having a plurality of separately expandable arcuate electrode portions, said stylet being axially movable within the inner lumen between a first position in which the distal end of the stylet is exposed from the distal cannula opening and a second position in which the distal end of the stylet is contained within the inner lumen; and a guide tube assembly dimensioned to be selectively received within the inner lumen and to be axially moveable therein, having a guide tube defining a central bore extending between and in fluid communication with a proximal opening and a side orifice, the guide tube being positionable within inner lumen so that the guide tube side orifice communicates with the side aperture of the cannula.

25. The system of claim 24, wherein the electrode is resiliently deformable from an expanded deployed configuration having a width greater than the outside dimension of the cannula to a contracted configuration having a width that is not greater than the inside dimension of the cannula passage, whereby the electrode is in the deployed configuration when the stylet is in the first position, and the electrode is in the contracted configuration when the stylet is in the second position.

26. The stylet of claim 25, wherein the electrode defines an arcuate cutting element extending from the distal end of the stylet.

27. The stylet of claim 26, wherein the electrode comprises first and second electrode portions that are resiliently deflectable radially inward when the electrode is resiliently deformed from the expanded deployed configuration to the contracted configuration.

28. A stylet for accessing tissue at a desired site within a patient's body, comprising:

an elongate shaft with an outside transverse dimension, a proximal end, a distal end, and an electrosurgical electrode disposed at the distal end of the elongate shaft having a plurality of separately expandable arcuate electrode portions and having an expanded deployed configuration with a width greater than the outside transverse dimension of the elongate shaft and a contracted configuration having a width that is less than the width of the expanded deployed configuration.

29. The stylet of claim 28, wherein the electrode comprises at least one arcuate cutting element which is spaced distally of the distal end of the elongate shaft and which lies in a plane that is substantially parallel to a longitudinal axis of the elongate shaft.

30. The stylet of claim 28, wherein the electrode comprises first and second electrode portions that are resiliently deflectable in an inward radial direction when the electrode is constricted from the expanded deployed configuration to the contracted configuration.

31. A system for accessing tissue at a desired site within a patient's body having a stylet which comprises:

an elongate shaft with an outside transverse dimension, a proximal end, a distal end having a recess configured to receive a portion of an electrode, and an electrosurgical electrode disposed at the distal end of the elongate shaft having a plurality of separately expandable arcuate electrode portions and an expanded deployed configuration with a width greater than the outside transverse dimension of the elongate shaft and a contracted configuration having a width that is less than the width of the expanded deployed configuration.

32. A system for accessing a subcutaneous tissue site in a patient's body, comprising:

a cannula having an inner lumen disposed between and in fluid communication with proximal and distal openings, the inner lumen having an inside transverse dimension and the cannula having an outside transverse dimension;

a longitudinally extending side aperture in the cannula near the distal opening and communicating with the inner lumen;

a biopsy device assembly dimensioned to be selectively received within the inner lumen and to be axially movable therein, having a stylet dimensioned to be slidably received in the inner lumen, terminating in a distal end with a recess configured to receive a portion of an electrode at which is located an electrosurgical electrode axially movable within the inner lumen between a first position in which the distal end of the stylet is exposed from the distal cannula opening and a second position in which the distal end of the stylet is contained within the inner lumen; and a guide tube assembly dimensioned to be selectively received within the inner lumen and to be axially moveable therein, having a guide tube defining a central bore extending between and in fluid communication with a proximal opening and a side orifice, the guide tube being positionable within inner lumen so that the guide tube side orifice communicates with the side aperture of the cannula.

33. A stylet for accessing tissue at a desired site within a patient's body, comprising:

an elongate shaft with an outside transverse dimension, a proximal end, a distal end, and a recess configured to receive a portion of an electrode, and an electrosurgical electrode disposed at the distal end of the elongate shaft having a plurality of separately expandable arcuate electrode portions and an expanded deployed configuration with a width greater than the outside transverse dimension of the elongate shaft and a contracted configuration having a width that is less than the width of the expanded deployed configuration, the electrode portions being resiliently deflectable in an inward radial direction when the electrode is constricted from an expanded deployed configuration to a contracted configuration.

* * * * *